US010781261B2

(12) United States Patent
Jansson et al.

(10) Patent No.: US 10,781,261 B2
(45) Date of Patent: *Sep. 22, 2020

(54) SUBCUTANEOUS FORMULATIONS OF ANTI-CD38 ANTIBODIES AND THEIR USES

(71) Applicant: Janssen Biotech, Inc., Horsham, PA (US)

(72) Inventors: Richard Jansson, Spring House, PA (US); Vineet Kumar, Spring House, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,994

(22) Filed: Apr. 10, 2019

(65) Prior Publication Data
US 2019/0330363 A1 Oct. 31, 2019

Related U.S. Application Data

(63) Continuation of application No. 15/366,474, filed on Dec. 1, 2016, now abandoned, which is a continuation-in-part of application No. 15/340,290, filed on Nov. 1, 2016, now Pat. No. 10,385,135.

(60) Provisional application No. 62/250,016, filed on Nov. 3, 2015.

(51) Int. Cl.
| | |
|---|---|
| C07K 16/28 | (2006.01) |
| A61K 39/395 | (2006.01) |
| A61K 9/00 | (2006.01) |
| A61K 47/26 | (2006.01) |
| A61K 31/573 | (2006.01) |
| A61K 38/47 | (2006.01) |
| A61K 9/08 | (2006.01) |
| A61K 39/00 | (2006.01) |

(52) U.S. Cl.
CPC ........ *C07K 16/2896* (2013.01); *A61K 9/0019* (2013.01); *A61K 31/573* (2013.01); *A61K 38/47* (2013.01); *A61K 39/39591* (2013.01); *A61K 47/26* (2013.01); *C12Y 302/01035* (2013.01); *A61K 9/08* (2013.01); *A61K 2039/505* (2013.01); *A61K 2039/545* (2013.01); *C07K 2317/21* (2013.01)

(58) Field of Classification Search
CPC ........ C07K 16/2896; C12Y 302/01035; A61K 9/0019
See application file for complete search history.

(56) References Cited

U.S. PATENT DOCUMENTS

| | | | |
|---|---|---|---|
| 6,737,056 B1 | 5/2004 | Presta | |
| 7,183,387 B1 | 2/2007 | Presta | |
| 7,223,397 B1 | 5/2007 | Rosenblum et al. | |
| 7,829,673 B2 | 11/2010 | DeWeers | |
| 7,829,693 B2 | 11/2010 | Kreutzer et al. | |
| 8,088,896 B2 | 1/2012 | Tesar et al. | |
| 8,153,765 B2 | 4/2012 | Park et al. | |
| 9,040,050 B2 | 5/2015 | Van De Winkel | |
| 9,603,927 B2 | 3/2017 | Doshi | |
| 9,732,154 B2 | 8/2017 | Doshi | |
| 10,385,135 B2 | 8/2019 | Janssen et al. | |
| 10,556,961 B2 | 2/2020 | Doshi | |
| 10,604,580 B2 | 3/2020 | Lokhorst | |
| 10,668,149 B2 | 6/2020 | Doshi et al. | |
| 2004/0141982 A1 | 7/2004 | Lust et al. | |
| 2004/0268425 A1 | 12/2004 | Bookbinder et al. | |
| 2006/0257397 A1 | 11/2006 | Throsby | |
| 2007/0148178 A1 | 6/2007 | Fyfe et al. | |
| 2008/0063642 A1 | 3/2008 | Adelman et al. | |
| 2008/0166344 A1 | 7/2008 | Nakahara et al. | |
| 2009/0076249 A1 | 3/2009 | Deweers et al. | |
| 2009/0148449 A1 | 6/2009 | DeWeers | |
| 2009/0304687 A1 | 12/2009 | Drachman | |
| 2009/0304710 A1 | 12/2009 | Park et al. | |
| 2010/0068136 A1 | 3/2010 | Hansen | |
| 2010/0092489 A1 | 4/2010 | van de Winkel et al. | |
| 2010/0285004 A1 | 11/2010 | Tesar et al. | |
| 2011/0044997 A1 | 2/2011 | Adler et al. | |
| 2011/0066111 A1 | 3/2011 | Teschner et al. | |
| 2011/0076273 A1 | 3/2011 | Adler et al. | |
| 2011/0099647 A1 | 4/2011 | De Weers et al. | |
| 2011/0293606 A1 | 12/2011 | Lejeune | |
| 2011/0300157 A1 | 12/2011 | Devy et al. | |
| 2012/0201827 A1 | 8/2012 | Elias | |
| 2012/0219551 A1 | 8/2012 | Johnson et al. | |
| 2012/0231008 A1 | 9/2012 | Guo et al. | |
| 2012/0244110 A1 | 9/2012 | Chen et al. | |
| 2012/0258081 A1 | 10/2012 | Corringham et al. | |
| 2012/0259095 A1 | 10/2012 | Beliard et al. | |
| 2012/0295864 A1 | 11/2012 | Taube et al. | |
| 2013/0109593 A1 | 5/2013 | Hartmann et al. | |
| 2013/0137134 A1 | 5/2013 | Mordechai et al. | |
| 2013/0209355 A1 | 8/2013 | De Weers et al. | |
| 2013/0302400 A1 | 11/2013 | Maneval et al. | |
| 2013/0309250 A1 | 11/2013 | Cogswell et al. | |
| 2013/0323247 A1 | 12/2013 | Zugmaier et al. | |
| 2014/0099254 A1 | 4/2014 | Chang et al. | |
| 2014/0155584 A1 | 6/2014 | Elias et al. | |
| 2014/0248238 A1 | 9/2014 | Wilson et al. | |
| 2014/0271644 A1 | 9/2014 | Elias et al. | |
| 2014/0356318 A1 | 12/2014 | Barken | |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

Notice of Allowance for U.S. Appl. No. 15/445,225 dated Mar. 25, 2020.

(Continued)

*Primary Examiner* — Jessica H Roark
(74) *Attorney, Agent, or Firm* — Hamilton, Brook, Smith & Reynolds, P.C.

(57) ABSTRACT

The present invention relates to subcutaneous formulations of anti-CD38 antibodies and their uses.

37 Claims, 2 Drawing Sheets

Specification includes a Sequence Listing.

(56) References Cited

U.S. PATENT DOCUMENTS

| | | |
|---|---|---|
| 2015/0118251 A1 | 4/2015 | Deslandes |
| 2015/0125447 A1 | 5/2015 | Heider |
| 2015/0231235 A1 | 8/2015 | Van De Winkel et al. |
| 2015/0246123 A1 | 9/2015 | Doshi |
| 2015/0246975 A1 | 9/2015 | Doshi |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer et al. |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2020/0002433 A1 | 1/2020 | Jansson et al. |
| 2020/0121588 A1 | 4/2020 | Campbell et al. |
| 2020/0223936 A1 | 7/2020 | Doshi et al. |
| 2020/0231697 A1 | 7/2020 | Jansson et al. |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 A1 | 12/2013 |
| EP | 2561868 A1 | 2/2013 |
| EP | 2567976 A2 | 3/2013 |
| JP | 2002-534396 A | 10/2002 |
| JP | 2008-533977 A | 8/2008 |
| JP | 2009-511033 A | 3/2009 |
| JP | 2010-504363 A | 2/2010 |
| JP | 2010-506582 A | 3/2010 |
| JP | 2014-509837 A | 4/2014 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 01/97844 A1 | 12/2001 |
| WO | WO 02/06347 A1 | 1/2002 |
| WO | WO 02/32288 A2 | 4/2002 |
| WO | WO 2003/106498 A2 | 12/2003 |
| WO | WO 2004/058288 A1 | 7/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/150530 A2 | 12/2008 |
| WO | WO 2009/062054 A1 | 5/2009 |
| WO | WO 2009/062504 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/154453 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/066450 A1 | 7/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/079150 A1 | 5/2017 |
| WO | WO 2018/002181 A1 | 1/2018 |
| WO | WO 2019/089832 A1 | 5/2019 |
| WO | WO 2019/186273 A1 | 10/2019 |

OTHER PUBLICATIONS

Notice of Allowance for U.S. Appl. No. 15/189,577 dated Mar. 31, 2020.

"A Prospective Phase II of Daratumumab in Previously Treated Systemic Light Chain (AL) Amyloidosis", published online at (http://cms.cws.net/content/beta.myelomasociety.org/files/2017ash/Roussel,%20Murielle-ASH2017.pdf (2017).

Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).

Adriouch et al., "Extracellular NAD+: a danger signal hindering regulatory T cells," Microbes and Infection, 14:1284-1292 (2012).

Agheli, A. et al., "A Rare Case of Primary Amyloidosis, Presenting with Severe Pulmonary Hypertension and Bilateral Pleural Effusion," Blood, vol. 106: p. 5100 (2005).

Arican, et al., "Philadelphia Chromosome (+) T-Cell Acute Lymphoblastic Leukemia After Renal Transplantation," Transplantation Proceedings, vol. 31; 3242-3243 (1999).

Armitage et al., "Long-Term Remission Durability and Functional Status of Patients Treated for Diffuse Histiocytic Lymphoma with the CHOP Regimen," J. Clin. Oncol. 2:898-902, (1984).

Arthur, "Innovations in subcutaneous infusions," J. Infus. Nurs. 38(3); 179-87; May/Jun. 2015.

Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).

Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).

Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.

Brand, F-X. et al., "Prospect for Anti-HER2 Receptor Therapy in Breast Cancer," AntiCancer Research, vol. 26; 463-470 (2006).

Brown, et al., "Tolerance of single, but not multiple, amino acid replacements in antibody VH CDR 2: a means of minimizing B cell wastage from somatic hypermutation?" The Journal of Immunology, 156: 3285-3291 (1996).

Carter et al., "Identification and validation of cell surface antigens for antibody targeting in oncology," Endocrine-Related Cancer, vol. 11, pp. 659-687, (2004).

(56) References Cited

OTHER PUBLICATIONS

Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCT02519452, Dec. 2017.

Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting*ANZMAP Multiple Myeloma Highlights*, 2017.

Chaulagain, C.P., et al., "How we Treat Systemic Light-Chain Amyloidosis," Clinical Advances in Hematology & Oncology, vol. 13; No. 5; 315-324 (2015).

Chen, et al., "Selection and Analysis of an Optimized Anti-VEGF Antibody: Crystal Structure of an Affinity-matured Fab in Complex with Antigen," Journal of Molecular Biology, 293: 865-881 (1999).

Cheson et al., "Revised Response Criteria for Malignant Lymphoma," Journal of Clinical Oncology, vol. 25, No. 5, 579-586 (Feb. 10, 2007).

Chillemi, A. et al., "Anti-CD38 Antibody Therapy: Windows of Opportunity Yielded by the Functional Characteristics of the Target Molecule," Molecular Medicine, vol. 19; 99-108 (2013).

Chou, et al., "Drug Combination Studies and their Synergy Quantification Using the Chou-Talalay Method," Cancer Research, 70(2): 440-446 (2010).

ClinicalTrials.gov "Study of YM155 in Refractory Diffuse Large B-cell Lymphoma (DLBCL) Subjects," Interventional Studies, U.S. National Library of Medicine, https://clinicaltrials.gov/ct2/show/record/NCT00498914, First posted Jul. 11, 2007 [retrieved on Sep. 10, 2018].

Colman, "Effects of amino acid sequence changes on antibody-antigen interactions," A Structural View of Immune Recognition by Antibodies, Biomolecular Research Institute, 33-36, (1994).

Cotner, et al., "Human T Cell Proteins Recognized by Rabbit Heteroantisera and Monoclonal Antibodies," International Journal of Immunopharmaceuticals, 3(3): 255-268 (1981).

Davies, et al., "Affinity improvement of single antibody VH domains: residues in all three hypervariable regions affect antigen binding," Immunotechnology, 2: 169-179 (1996).

Davis, et al., "Transgenic mice as a source of fully human antibodies for the treatment of cancer," Cancer and Metastasis Reviews, 18: 421-425 (1999).

Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. vol. 20, No. 17, pp. 4574-4583 (2014).

Dennis, "Off by a Whisker," Nature, 442 (17): 749-741 (2006).

DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).

De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).

De Weers, M. et al., "Humax-CD38, a New Human CD38 Monoclonal Antibody, Effectively Mediates Killing of Multiple Killing of Multiple Myeloma and Plasma Cell Leukemia Cells," abstract, Submitted for the 16th European Congress of Immunology—ECI2006, Paris, France, [Sep. 6-9, 2006].

De Weers et al., "HuMax-CD38, a new human CD38 monoclonal antibody, effectively mediates killing of multiple myeloma and plasma cell leukemia cells," The 23rd International Conference on 'Advances in the Application of Monoclonal Antibodies in Clinical Oncology, (Jun. 26-28, 2006), Royal Myconian Resort & Thalasso Spa Center, Mykonos, Greece (Abstract).

Dimopoulos, M.A. et al., "Daratumumab, Lenalidomide, and Dexamethasone for Multiple Myeloma," The New England Journal of Medicine, vol. 375; No. 14; 1319-1331 (2016).

Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).

Dos Santos, et al., Anti-Leukemic Activity of Daratumumab in Acute Myeloid Leukemia Cells and Patient-Derived Xenografts, Blood, vol. 124, Abstract 2312, (2014).

Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).

Ellis, et al., "Engineered Anti-CD38 Monoclonal Antibodies for Immunotherapy of Multiple Myeloma," The Journal of Immunology, 155: 925-937 (1995).

Eldfors, et al., "Landscape of Mutations in Relapsed Acute Myeloid Leukemia," vol. 124: No. 21, p. 2367; (2014).

Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).

Ferrero, et al., Characterization and phylogenetic epitope mapping of CD38 ADPR cyclase in the cynomolgus macaque, BMC Immunology, 5(21): 1-13 (2004).

Field-Smith, "Bortezomid (Velcade™) in the treatment of multiple myeloma," Therapeutic and Clinical Risk Management, 2(3): 271-279 (2006).

Flavell, et al., "Therapy of human T-cell acute lymphoblastic leukaemia with a combination of anti-CD7 and anti-CD38-Saporin immunotoxins is significantly better than therapy with each individual immunotoxin," Br. J. Cancer, vol. 84, No. 4, pp. 571-578, (2001).

Franco, et al., "The transmembrane glycoprotein CD38 is a catalytically active transporter responsible for generation and influx of the second messenger cyclic ADP-ribose across membranes," FASEB Journal, 12: 1507-1520 (1998).

Fujimori, et al., "A Modeling Analysis of Monoclonal Antibody Percolation Though Tumors: A Binding-Site Barrier," Journal of Nucleic Medicine, 31: 1191-1198 (1990).

Funaro et al., "CD38 Functions Are Regulated Through an Internalization Step," Journal of Immunology, 160: 2238-2247 (1998).

Funaro, et al., "Human CD38: a versatile leukocyte molecule with emerging clinical prospectives," Fundamental and Clinical Immunology, 3(3): 101-113 (1995).

Funaro, et al., "Identification and characterization of an active soluble form of human CD38 in normal and pathological fluids," International Immunology, 8(11): 1643-1650 (1996).

Funaro, et al., "Involvement of the Multilineage CD38 Molecule in a Unique Pathway of Cell Activation and Proliferation," The Journal of Immunology, 145: 2390-2396 (1990).

Gallo, et al., "The human immunoglobulin loci introduced into mice: V(D) and J gene segment usage similar to that of adult humans," European Journal of Immunology, 30: 534-540 (2000).

Genmab "Humanx-CD38 Effective in Preclinical Studies," Genmab A/S, Stock Exchange Release 57/2005.

Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b 4199069/18%20Daratumumab%20breakthrough%20status_010513_uk.pdf, (May 1, 2013).

Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).

George, et al., "Differential Effects of Anti-β2-Glycoprotein I Antibodies on Endothelial Cells and on the Manifestations of Experimental Antiphospholipid Syndrome," Circulation, 97: 900-906 (1998).

Goldmacher, et al., "Anti-CD38-Blocked Ricin: An immunotoxin for the Treatment of Multiple Myeloma," The American Society of Hematology, 84(9): 3017-3025 (1994).

(56) References Cited

OTHER PUBLICATIONS

Goodwin, "Subcutaneous Daratumumab Potential Game Changer for Multiple Myeloma," Oncology Times, 2017 American Society of Hematology Annual Meeting, p. 49, (2017).
Gopalakrishnan, et al. "Daratumumab improves the anti-myeloma effect of newly emerging multidrug therapies," Blood and Lymphatic Cancer: Targets and Therapy, 3: 19-24 (2013).
Graeff, et al., "Enzymatic Synthesis and Characterizations of Cyclic GDp-ribose," The Journal of Biological Chemistry, 269(48): 30260-30267 (1994).
Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Guse et al., "Regulation of calcium signaling in T lymphocytes by the second messenger cyclic ADP-ribose," Nature 398:70-73, (1999).
Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-eonjugated Monoclonal Antibody 212Bi-anti-Tac, Cancer Research, 54: 4362-4370 (1994).
Henry, et al., "The use of basiliximab in solid organ transplantation," Expert Opinion Pharmacotherapy, 3(10): 1657-1663 (2002).
Holm, et al., "Functional mapping and single chain construction of the anti-cytokeratin 8 monoclonal antibody TS1," Molecular Immunology, 44: 1075-1084 (2017).
Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Jackisch, et al., "Subcutaneous versus intravenous formulation of trastuzumab for HER2-positive early breast cancer: updated results from the phase III HannaH study," Annals of Oncology, vol. 26, pp. 320-325, (2015).
Jackson, et al., "Isolation of a cDNA Encoding the Human CD38 (T10) molecule, A Cell Surface Glycoprotein With an Unusual Discontinuous Pattern of Expression During Lymphocyte Differentiation," The Journal of Immunology, 144(7): 2811-2815 (1990).
Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) 41st Annual meeting, (Jun. 4, 2018).

Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "The long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Kreuger, et al., Successful in vivo blockade of CD25 (high-affinity interleukin 2 receptor) on T cells by administration of humanized anti-Tac antibody to patients with psoriasis, Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).
Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).

(56) References Cited

OTHER PUBLICATIONS

Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Leveque "Subcutaneous Administration of Anticancer Agents" Anticancer Research, Departments of Pharmacy, University Hospital, Strasbourg, France, vol. 34, pp. 1579-1586 (2014).
Li, et al., "Creation of Patient Derived AML Xenografts Displaying Distinct Phenotypes and Geneotypes," Blood, vol. 122: No. 21, p. 5018 (2013).
Lin, et al., "Structure-Function Relationships in Glucagon: Properties of Highly Purified Des-His1-, Monoiodi-, and [Des-Asn28,Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS ONE, vol. 9, No. 1, p. Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Malavasi, et al., "Human CD 38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
Mauri, C. and Menon, M., "The expanding family of regulatory B cells," International Immunology, vol. 27; No. 10; 479-486 (2015).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).
Mills, et al., Characterization of Monoclonal Antibodies that Inhibit CD38 ADp-ribosyl Cyclase Activity, LSSURP HLB Program, Department of Pharmacology, University of Minnesota, 2007.
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCL5," Journal for Immunotherapy of Cancer, Nov. 6, 2014, vol. 2, p. 110-112
Nijhof, et al.,"Modulation of CD 38 Expression Levels on Multiple Myeloma Tumor Cells By All-Trans Retinoic Acid Improves the Efficacy of the Anti-CD 38 Monoclonal Antibody Daratumumab," Blood, American Society of Hematology, US, vol . 124, No. 21, p. 2096, Dec. 6, 2014. (Abstract Only)
Nijhof, I.S. et al., Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pp. Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., Nov. 14, 2014, vol. 21, No. 12, pp. 2802-2810.
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor α Monoclonal Antibody)," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, Jun. 26, 2006.
Parren, et al., HuMax-CD38, Torino, Jun. 8-10, 2006.
Pascual, et al. "Anti-interleukin-2 receptor antibodies: basiliximab and daclizumab" Nephrology Dial. Transplant, 16: 1756-1760 (2001).
Patton, D.T. et al., "The P13K p110δ Regulates Expression of CD38 on Regulatory T Cells," PLOS one, vol. 6; No. 3; e17359; 8 pages (2011).
Paul, M.D., "Fundamental Immunology," Chapter 9, Raven Press, New York, 3rd ed., 292-295 (1993).
Peipp, et al., "Fully Human CD38 Antibodies Efficiently Trigger ADCC and CDC of Multiple Myeloma Cell Lines and Primary Tumor Cells (Poster)," Blood, vol. 106(11): 944A, 47th Annual Meeting of the American Society of Hematology, 2005; published (Nov. 16, 2005).
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).
Peipp, et al., 47th Annual Meeting of the American Society of Hematology, Atlanta, GA, Dec. 10-13, 2005. (Meeting Abstract).
Peng, et al., "Oncolytic measles viruses displaying a single-chain antibody against CD38, a myeloma cell marker," Blood, 101, 2557-2562 (2003).

(56) References Cited

OTHER PUBLICATIONS

Phase 1/2 Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Richardson, et al., "Daratumumab," Drugs of the Future, 38(8): 545-554 (2013).
Rituxan Hycela Label, "Highlights of prescribing information. RITUXAN HYCELA™ (rituximab and hyaluronidase human) injection, for subcutaneous use," 32 pages (Jun. 2017).
Sachchithanantham, S. et al., "Use of Plasma Cell Immunophenotype as Prognostic Markers in Patients with Systemic AL Amyloidosis," Blood, vol. 122; p. 3120 (2013).
Salar et al., "Comparison of Subcutaneous Versus Intravenous Administration of Rituximab As Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).
Sher, T. et al., "First report of safety and efficacy of daratumumab in 2 cases of advanced immunoglobulin light chain amyloidosis," Blood, vol. 128; No. 15; 1987-1989 (2016).
Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, (2001).
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Skeel, Handbook of Cancer Gliemotherapy, 3rd edition, Little, Brown & Co., pp. 330-350 (1991).
Sonneveld, P. and Annemiek Broijl, "Treatment of Relapsed and Refractory Multiple Myeloma," Review Article, Leaders in Hematology, review series, Haematologica, 101(4):396-406 (2016).
Spencer, A. et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
Strome, S.E. et al., "A Mechanistic Perspective of Monoclonal Antibodies in Cancer Therapy Beyond Target-Related Effects," The Oncologist, vol. 12; 1084-1095 (2007).
Tabernero, et al., "Adult precursor B-ALL with BCR/ABL gene rearrangements displays a unique immunophenotype based on the pattern of CD10, CD34, CD13, and CD38 expression," Leukemia, vol. 15, No. 3, pp. 406-414, (2001).
Talmadge, J.E. and Gabrilovich, D.I, "History of myeloid-derived suppressor cells," Nature Reviews, vol. 13; 739-752 (2013).
Terhorst, et al., "Biochemical Studies of the Human Thymocyte Cell-Surface Antigens T6, T9 and T10," Cell, 23: 771-780 (1981).
Topalian, S.L., et al., "Immune Checkpoint Blockade: A Common Denominator Approach to Cancer Therapy," Cancer Cell, vol. 27; 450-461 (2015).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).
Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Van Bueren, et al., "Direct In Vitro Comparison of Daratumumab With Surrogate Analogs of Anti-CD38 Antibodies," New Evidence Oncology Issue, Apr. 2015 [retrieved on Feb. 3, 2016] Retrieved from the Internet: URL: Http:///www.newevidence.com/oncology/direct-in-vitro-comparison-of-daratumumab-with-surrogate-analogs-of-anti-cd38-antibodies>.
Van de Donk et al., "Monoclonal antibodies targeting CD38 in hematological malignancies and beyond," Immunological Reviews, vol. 270, pp. 95-112, (2016).
Venner et al., Cyclophosphamide, bortezomib, and dexamethasone therapy in AL amyloidosis is associated with high clonal response rates and prolonged progression-free survival, Blood, vol. 119, No. 9, pp. 4387-4390, (2012).
Vorre, et al., "Multiple Daratumumab Abstracts to be Presented at EHA," ArrayDiagnostica, Abstract Only (2014).
Wagner, V., et al., "Preclinical Efficacy of Sepantronium Bromide (YM155) in multiple myeloma is conferred by down regulation of Mcl-1," Oncotarget, 5(21): 10237-10250 (2014).
Wagner et al., Survivin in Multiple Myeloma: Prognostic and Therapeutic Implications, vol. 118, Article 137, 2011 (Abstract Only).
WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).
Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).
Ye et al, "Abstract P240: Treg Increases HepG2 Cell Growth by RANK-RANKL pathway." Journal for Immunotherapy of Cancer, vol. 2; Suppl 3; p. 240 (Nov. 6, 2014).
International Search Report and Written Opinion dated Feb. 12, 2019 for International Application No. PCT/US2018/058561, entitled "Methods of Treating High Risk Multiple Myeloma".
International Preliminary Report on Patentability dated May 8, 2018 for International Application No. PCT/US2016/59893, entitled "Subcutaneous Formulations of Anti-CD38 Antibodies and Their Uses".
International Search Report and Written Opinion dated Jan. 24, 2017 for International Application No. PCT/US2016/59893, entitled "Subcutaneous Formulations of Anti-CD38 Antibodies and Their Uses".
International Preliminary Report on Patentability dated Dec. 26, 2017 for International Application No. PCT/US2016/038702, entitled "Combination Therapies for Heme Malignancies With Anti-CD38 Antibodies and Survivin Inhibitors".
International Search Report and Written Opinion dated Nov. 29, 2016 for International Application No. PCT/US2016/038702, entitled "Combination Therapies for Heme Malignancies With Anti-CD38 Antibodies and Survivin Inhibitors".
International Preliminary Report on Patentability dated Mar. 14, 2017 for International Application No. PCT/US2015/048899, entitled "Combination Therapies With Anti-CD38 Antibodies".
International Search Report and Written Opinion dated Apr. 8, 2016 for International Application No. PCT/US2015/048899, entitled "Combination Therapies With Anti-CD38 Antibodies".
International Preliminary Report on Patentability dated Nov. 21, 2017 for International Application No. PCT/US2016/033544, entitled "Anti-CD38 Antibodies for Treatment of Light Chain Amyloidosis and Other CD38-Positive Hematological Malignancies".

(56) References Cited

OTHER PUBLICATIONS

International Search Report and Written Opinion dated Oct. 24, 2016 for International Application No. PCT/US2016/033544, entitled "Anti-CD38 Antibodies for Treatment of Light Chain Amyloidosis and Other CD38-Positive Hematological Malignancies".
International Preliminary Report on Patentability dated Jun. 6, 2016 for International Application No. PCT/US2015/063371, entitled "Anti-CD38 Antibodies for Leukemia".
International Search Report and Written Opinion dated Feb. 19, 2016 for International Application No. PCT/US2015/063371, entitled "Anti-CD38 Antibodies for Treatment of Acute Myeloid Leukemia".
International Preliminary Report on Patentability dated Dec. 26, 2017 for International Application No. PCT/US2016/039165, entitled "Immune Modulation and Treatment of Solid Tumors With Antibodies That Specifically Bind CD3 8".
International Search Report and Written Opinion dated Oct. 14, 2016 for International Application No. PCT/US2016/039165, entitled "Immune Modulation and Treatment of Solid Tumors With Antibodies That Specifically Bind CD3 8".
International Preliminary Report on Patentability dated Sep. 6, 2016 for International Application No. PCT/US2015/017425, entitled "Anti-CD38 Antibodies for Treatment of Acute Lymphoblastic Leukemia".
International Search Report and Written Opinion dated Sep. 21, 2015 for International Application No. PCT/US2015/017425, entitled "Anti-CD38 Antibodies for Treatment of Acute Lymphoblastic Leukemia".
International Search Report and Written Opinion dated Sep. 25, 2017 for International Application No. PCT/EP2017/066063, entitled "Treatment of IgE-Mediated Diseases With Antibodies That Specifically Bind CD38".
International Preliminary Report on Patentability dated Sep. 6, 2016 for International Application No. PCT/US2015/017420, entitled "Combination Therapies With Anti-CD38 Antibodies".
International Search Report and Written Opinion dated Jul. 8, 2015 for International Application No. PCT/US2015/017420, entitled "Combination Therapies With Anti-CD38 Antibodies".
Intellectual Property Office of Singapore Written Opinion dated Apr. 17, 2018 for Application No. 11201701867S, entitled "Combination Therapies with Anti-CD38 Antibodies ".
Supplementary European Search Report dated Feb. 21, 2018 for European Application No. EP 15839752 , entitled "Combination Therapies with Anti-CD38 Antibodies".
Non Final Office Action for U.S. Appl. No. 15/340,290 dated Nov. 20, 2017.
Final Office Action for U.S. Appl. No. 15/340,290 dated May 16, 2018.
Non Final Office Action for U.S. Appl. No. 15/340,290 dated Oct. 10, 2018.
Non Final Office Action for U.S. Appl. No. 15/366,474 dated Nov. 20, 2017.
Final Office Action for U.S. Appl. No. 15/366,474 dated May 16, 2018.
Applicant Initiated Interview for U.S. Appl. No. 15/366,474 dated Sep. 17, 2018.
Non Final Office Action for U.S. Appl. No. 15/366,474 dated Oct. 11, 2018.
Non Final Office Action for U.S. Appl. No. 15/189,577 dated Oct. 31, 2017.
Final Office Action for U.S. Appl. No. 15/189,577 dated Apr. 13, 2018.
Non Final Office Action for U.S. Appl. No. 15/189,577 dated Sep. 28, 2018.
Non Final Office Action for U.S. Appl. No. 14/847,428 dated Sep. 23, 2016.
Non Final Office Action for U.S. Appl. No. 15/386,391 dated Jun. 18, 2018.
Non Final Office Action for U.S. Appl. No. 15/160,476 dated Sep. 15, 2017.
Non Final Office Action for U.S. Appl. No. 15/160,476 dated Nov. 5, 2018.
Final Office Action for U.S. Appl. No. 15/160,476 dated Apr. 23, 2018.
Non Final Office Action for U.S. Appl. No. 14/956,890 dated Nov. 25, 2016.
Final Office Action for U.S. Appl. No. 14/956,890 dated Jul. 24, 2018.
Non Final Office Action for U.S. Appl. No. 15/340,214 dated May 16, 2018.
Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
Final Office Action for U.S. Appl. No. 15/445,225 dated Dec. 17, 2018.
Non Final Office Action for U.S. Appl. No. 15/651,333 dated Sep. 27, 2018.
Final Office Action for U.S. Appl. No. 15/386,391 dated Dec. 28, 2018.
Final Office Action for U.S. Appl. No. 14/956,890 dated Jan. 14, 2019.
Notice of Allowance for U.S. Appl. No. 15/651,333 dated Feb. 21, 2019.
Notice of Allowance for U.S. Appl. No. 15/189,577 dated Mar. 5, 2019.
Final Office Action for U.S. Appl. No. 15/340,290 dated Mar. 11, 2019.
Notice of Allowance for U.S. Appl. No. 15/386,391 dated Mar. 29, 2019.
Notice of Allowance for U.S. Appl. No. 15/340,290 dated May 22, 2019.
Notice of Allowance for U.S. Appl. No. 15/651,333 dated May 31, 2019.
Final Office Action for U.S. Appl. No. 15/160,476 dated Jun. 14, 2019.
ClinicalTrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015.
ClinicalTrials.gov, "A Study to Evaluate Subcutaneous Daratumumab in Combination with Standard Multiple Myeloma Treatment Regimens," Identifier: NCT03412565, First Posted: Jan. 26, 2018 (16 pages).
Fujioka, Y. and Kurokawa, M., "Follicular lymphoma presenting with massive splenomegaly," International J Hematol, vol. 95; 3-4 (2012).
Kaufman, G.P. et al., "Daratumumab yields rapid and deep hematologic responses in patients with heavily pretreated AL amyloidosis," Blood, vol. 130; No. 7; 900-902 (2017).
Machida, H. et al., "Aggressive plasma cell leukemia with cleaved, multilobated and monocytoid nuclei," International Journal of Hematol., vol. 73; Suppl 1; 158; Abstract No. 411 (2001).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. p. 340 (2002).
Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).
Ryan, A. et al., "Potentiation of Anti-Myeloma Activity of Daratumumab with Combination of Cyclophosphamide, Lenalidomide or Bortezomib via a Tumor Secretory Response That Greatly Augments Macrophage-Induced ADCP," Annual Meeting at the Haematology Association of Ireland, Oct. 15, 2016; 20 pages.

(56) References Cited

OTHER PUBLICATIONS

Saito, M. et al., "A Case of Retroperitoneal Extramedullary Plasmacytoma," Acta Urol. Jpn., vol. 49; 735-739 (2003).
Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).
Usmani, S.Z. et al., "Subcutaneous delivery of daratumumab in relapsed or refractory multiple myeloma," Blood, vol. 134; No. 8; 668-677 (2019).
International Preliminary Report on Patentability dated Jan. 10, 2019 for International Application No. PCT/EP2017/066063, entitled "Treatment of IgE-Mediated Diseases With Antibodies That Specifically Bind CD38".
Notice of Allowance for U.S. Appl. No. 15/189,577 dated Dec. 19, 2019.
Non Final Office Action for U.S. Appl. No. 15/160,476 dated Dec. 20, 2019.
Final Office Action for U.S. Appl. No. 14/956,890 dated Jan. 7, 2020.
Non-Final Office Action for U.S. Appl. No. 15/798,670 dated Jan. 22, 2020.
English translation of Office Action for JP Application No. 2016-554350, dated Nov. 27, 2018.
Abdi, J. et al., "Drug resistance in multiple myeloma: latest findings and new concepts on molecular mechanisms," Oncotarget, vol. 4; No. 12; 2186-2207 (2013).
Chaulagain, C.P. and Comenzo, R.L., "New Insights and Modern Treatment of AL Amyloidosis," Curr Hematol Malig Rep, vol. 8; 291-298 (2013).
Chiarugi, A. et al., "The NAD metabolome—a key determinant of cancel cell biology," Nature Reviews, vol. 12; 741-752 (2012).
Comenzo, R.L. et al., "Consensus guidelines for the conduct and reporting of clinical trials in systemic light-chain amyloidosis," Leukemia, vol. 26; 2317-2325 (2012).
Ettinger, R. et al., "Pathogenic mechanisms of IgE-mediated inflammation in self-destructive autoimmune responses," Autoimmunity, vol. 50; No. 1; 25-36 (2017).
Gupta, R. et al., "The Economic Impact of Childhood Food Allergy in the United States," JAMA Pediatrics, vol. 167; No. 11; 1026-1031 (2013).
Holgate, S.T., "New strategies with anti-IgE in allergic diseases," World Allergy Organization Journal, vol. 7; No. 17; 6 pages (2014).
Inaba, H. et al., "Acute lymphoblastic leukaemia," Lancet, vol. 381; 27 pages (2013).
Lepenies, B. and Jacobs, T., "The Role of Negative Costimulators During Parasitic Infections," Endocrine, Metabolic & Immune Disorders—Drug Targets, vol. 8; 279-288 (2008).
Manier, S. et al., "Bone Marrow Microenvironment in Multiple Myeloma Progession," Journal of Biomedicine and Biotechnology, vol. 2012; 5 pages (2012).
Merlini, G. and Bellotti, V., "Molecular Mechanisms of Amyloidosis," The New England Journal of Medicine, vol. 349; No. 6; 583-596 (2003).
Mills, E.N.C. et al., "The prevalence, cost and basis of food allergy across Europe," Allergy, vol. 62; 717-722 (2007).
Patel, J.P., "Prognostic Relevance of Integrated Genetic Profiling in Acute Myeloid Leukemia," The New England Journal of Medicine, vol. 366; No. 12; 1079-1089 (2012).

Sicherer, S.H. and Sampson, H.A., "Food allergy: Epidemiology, pathogenesis, diagnosis, and treatment," J. Allergy Clin Inmmunol, vol. 133; 291-307 (2014).
Swaika, A. et al., "Current state of anti-PD-L1 and anti-PD-1 agents in cancer therapy," Molecular Immunology, vol. 67; 4-17 (2015).
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Wang, L. et al., "VISTA, a novel mouse Ig superfamily ligand that negatively regulates T cell responses," J. Exp. Med., vol. 208; No. 3; 577-592 (2011).
Wei, W. et al., "Roles and mechanisms of the CD38/cyclic adenosine diphosphate ribose/Ca2+ signaling pathway," World Journal of Biological Chemistry, vol. 5; No. 1; 58-67 (2014).
Notice of Allowance for U.S. Appl. No. 15/445,225 dated Jul. 29, 2019.
Notice of Allowance for U.S. Appl. No. 15/386,391 dated Jul. 30, 2019.
Non-Final Office Action for U.S. Appl. No. 14/956,890 dated Jul. 30, 2019.
Notice of Allowance for U.S. Appl. No. 15/189,577 dated Sep. 12, 2019.
Notice of Allowance for U.S. Appl. No. 15/651,333 dated Oct. 9, 2019.
ClinicalTrials.gov, "Daratumumab in Combination with ATRA (DARA/ATRA)," Identifier: NCT02751255; First posted: Apr. 26, 2016.
Notice of Allowance for U.S. Appl. No. 15/386,391 dated Nov. 18, 2019.
Of Allowance for U.S. Appl. No. 15/445,225 dated Dec. 4, 2019.
ClinicalTrials.gov, "A Phase 1 Study to Assess the Safety, Tolerability, and Pharmacokinetics of TAK-079 in Healthy Participants," Identifier: NCT02219256, 13 pages; Latest version posted: Mar. 22, 2017. (13 pages).
Dispenzieri, A. et at., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).
Smithson, G. et al.,"TAK-079 is a high affinity monoclonal antibody that effectively mediates CD38+ cell depletion," Journal of Immunol., vol. 198; Suppl. 1; 224.20; Abstract (2017).
International Preliminary Report on Patentability dated May 14, 2020 for International Application No. PCT/US2018/058561, entitled "Methods of Treating High Risk Multiple Myeloma".
International Search Report and Written Opinion dated Apr. 24, 2020 for International Application No. PCT/US2019/056838, entitled "Method of Providing Subcutaneous Administration of Anti-CD38 Antibodies".
Notice of Allowance for U.S. Appl. No. 15/160,476 dated May 4, 2020.
Notice of Allowance for U.S. Appl. No. 16/460,754 dated May 18, 2020.
Notice of Allowance for U.S. Appl. No. 15/445,225 dated Jul. 15, 2020.
Notice of Allowance for U.S. Appl. No. 14/956,890 dated Jul. 29, 2020.
Mateos et al., "Subcutaneous versus intravenous daratumumab in patients with relapsed or refractory multiple myeloma (COLUMBA): a multicentre, open-label, non-inferiority, randomised, phase 3 trial," *Lancet Haematol.* 7(5): e370-e380 (2020), www.thelancet.com/haematology, Published online Mar. 23, 2020.

SEQUENCE LISTING

<160> NUMBER OF SEQ ID NOS: 22

<210> SEQ ID NO 1
<211> LENGTH: 300
<212> TYPE: PRT
<213> ORGANISM: Homo sapiens

```
<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
            210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens
```

```
<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: daratumumab VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: daratumumab VL

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: daratumumab HCDR1
```

```
<400> SEQUENCE: 6

Ser Phe Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: Daratumumab HCDR2

<400> SEQUENCE: 7

Ala Ile Ser Gly Ser Gly Gly Gly Thr Tyr Tyr Ala Asp Ser Val Lys
1               5                   10                  15

Gly

<210> SEQ ID NO 8
<211> LENGTH: 13
<212> TYPE: PRT
<213> ORGANISM: Artificial Sequence
<220> FEATURE:
<223> OTHER INFORMATION: Daratumumab HCDR3

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Daratumumab LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: DASNRAT

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Daratumumab LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: Daratumumab heavy chain
```

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

-continued

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: Daratumumab light chain

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 122
<212> TYPE: PRT
<213> ORGANISM: Artificial Sequence
<220> FEATURE:
<223> OTHER INFORMATION: mAb 003 VH

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

```
Gly Arg Val Ile Pro Phe Leu Gly Ile Ala Asn Ser Ala Gln Lys Phe
 50                  55                  60

Gln Gly Arg Val Thr Ile Thr Ala Asp Lys Ser Thr Ser Thr Ala Tyr
 65                  70                  75                  80

Met Asp Leu Ser Ser Leu Arg Ser Glu Asp Thr Ala Val Tyr Tyr Cys
                 85                  90                  95

Ala Arg Asp Asp Ile Ala Ala Leu Gly Pro Phe Asp Tyr Trp Gly Gln
                100                 105                 110

Gly Thr Leu Val Thr Val Ser Ser Ala Ser
            115                 120
```

<210> SEQ ID NO 15
<211> LENGTH: 107
<212> TYPE: PRT
<213> ORGANISM: Artificial Sequence
<220> FEATURE:
<223> OTHER INFORMATION: mAb 003 VL

<400> SEQUENCE: 15

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105
```

<210> SEQ ID NO 16
<211> LENGTH: 122
<212> TYPE: PRT
<213> ORGANISM: Artificial Sequence
<220> FEATURE:
<223> OTHER INFORMATION: mAb024 VH

<400> SEQUENCE: 16

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Ser Asn Tyr
                 20                  25                  30

Trp Ile Gly Trp Val Arg Gln Met Pro Gly Lys Gly Leu Glu Trp Met
             35                  40                  45

Gly Ile Ile Tyr Pro His Asp Ser Asp Ala Arg Tyr Ser Pro Ser Phe
 50                  55                  60

Gln Gly Gln Val Thr Phe Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg His Val Gly Trp Gly Ser Arg Tyr Trp Tyr Phe Asp Leu Trp
                100                 105                 110

Gly Arg Gly Thr Leu Val Thr Val Ser Ser
            115                 120
```

```
-continued

<210> SEQ ID NO 17
<211> LENGTH: 107
<212> TYPE: PRT
<213> ORGANISM: Artificial Sequence
<220> FEATURE:
<223> OTHER INFORMATION: mAb 024 VL

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Gly Leu Leu Ile
        35                  40                  45

Tyr Asp Ala Ser Asn Arg Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 18
<211> LENGTH: 120
<212> TYPE: PRT
<213> ORGANISM: Artificial Sequence
<220> FEATURE:
<223> OTHER INFORMATION: MOR202 VH

<400> SEQUENCE: 18

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 19
<211> LENGTH: 109
<212> TYPE: PRT
<213> ORGANISM: Artificial Sequence
<220> FEATURE:
<223> OTHER INFORMATION: MRO202 VL

<400> SEQUENCE: 19

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30
```

```
Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
                 85                  90                  95

Val Phe Gly Gly Gly Thr Lys Leu Thr Val Leu Gly Gln
                100                 105

<210> SEQ ID NO 20
<211> LENGTH: 120
<212> TYPE: PRT
<213> ORGANISM: Artificial Sequence
<220> FEATURE:
<223> OTHER INFORMATION: Isatuximab VH

<400> SEQUENCE: 20

Gln Val Gln Leu Val Gln Ser Gly Ala Glu Val Ala Lys Pro Gly Thr
 1               5                  10                  15

Ser Val Lys Leu Ser Cys Lys Ala Ser Gly Tyr Thr Phe Thr Asp Tyr
             20                  25                  30

Trp Met Gln Trp Val Lys Gln Arg Pro Gly Gln Gly Leu Glu Trp Ile
         35                  40                  45

Gly Thr Ile Tyr Pro Gly Asp Gly Asp Thr Gly Tyr Ala Gln Lys Phe
     50                  55                  60

Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
                100                 105                 110

Gly Thr Ser Val Thr Val Ser Ser
            115                 120

<210> SEQ ID NO 21
<211> LENGTH: 107
<212> TYPE: PRT
<213> ORGANISM: Artificial Sequence
<220> FEATURE:
<223> OTHER INFORMATION: Isatuximab VL

<400> SEQUENCE: 21

Asp Ile Val Met Thr Gln Ser His Leu Ser Met Ser Thr Ser Leu Gly
 1               5                  10                  15

Asp Pro Val Ser Ile Thr Cys Lys Ala Ser Gln Asp Val Ser Thr Val
             20                  25                  30

Val Ala Trp Tyr Gln Gln Lys Pro Gly Gln Ser Pro Arg Arg Leu Ile
         35                  40                  45

Tyr Ser Ala Ser Tyr Arg Tyr Ile Gly Val Pro Asp Arg Phe Thr Gly
     50                  55                  60

Ser Gly Ala Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys
                100                 105
```

```
<210> SEQ ID NO 22
<211> LENGTH: 509
<212> TYPE: PRT
<213> ORGANISM: Artificial Sequence
<220> FEATURE:
<223> OTHER INFORMATION: rHuPH20

<400> SEQUENCE: 22

Met Gly Val Leu Lys Phe Lys His Ile Phe Phe Arg Ser Phe Val Lys
1               5                   10                  15

Ser Ser Gly Val Ser Gln Ile Val Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365
```

-continued

```
Val Thr Leu Ala Ala Lys Met Cys Ser Gln Val Leu Cys Gln Glu Gln
    370             375             380
Gly Val Cys Ile Arg Lys Asn Trp Asn Ser Ser Asp Tyr Leu His Leu
385             390             395             400
Asn Pro Asp Asn Phe Ala Ile Gln Leu Glu Lys Gly Gly Lys Phe Thr
            405             410             415
Val Arg Gly Lys Pro Thr Leu Glu Asp Leu Glu Gln Phe Ser Glu Lys
            420             425             430
Phe Tyr Cys Ser Cys Tyr Ser Thr Leu Ser Cys Lys Glu Lys Ala Asp
        435             440             445
Val Lys Asp Thr Asp Ala Val Asp Val Cys Ile Ala Asp Gly Val Cys
    450             455             460
Ile Asp Ala Phe Leu Lys Pro Pro Met Glu Thr Glu Glu Pro Gln Ile
465             470             475             480
Phe Tyr Asn Ala Ser Pro Ser Thr Leu Ser Ala Thr Met Phe Ile Val
                485             490             495
Ser Ile Leu Phe Leu Ile Ile Ser Ser Val Ala Ser Leu
            500             505
```

SUBCUTANEOUS FORMULATIONS OF ANTI-CD38 ANTIBODIES AND THEIR USES

CROSS-REFERENCE TO RELATED APPLICATIONS

This application is a continuation of U.S. patent application Ser. No. 15/366,474, filed 1 Dec. 2016, which is a continuation-in-part of U.S. patent application Ser. No. 15/340,290, filed 1 Nov. 2016, which claims the benefit of U.S. Provisional Application Ser. No. 62/250,016, filed 3 Nov. 2015, the entire contents of which are incorporated herein by reference.

SEQUENCE LISTING

This application contains a Sequence Listing submitted via EFS-Web in application Ser. No. 15/366,474 on Dec. 1, 2016, the entire content of which is incorporated herein by reference in its entirety. The ASCII text file, created on 1 Dec. 2016, is named JBI5070USNPSEQLIST.txt and is 26 kilobytes in size.

FIELD OF THE INVENTION

The present invention relates to subcutaneous formulations of anti-CD38 antibodies and their uses.

BACKGROUND OF THE INVENTION

CD38 is a multifunctional protein having function in receptor-mediated adhesion and signaling as well as mediating calcium mobilization via its ecto-enzymatic activity, catalyzing formation of cyclic ADP-ribose (cADPR) and ADPR. CD38 mediates cytokine secretion and activation and proliferation of lymphocytes (Funaro et al., J Immunol 145:2390-6, 1990; Terhorst et al., Cell 771-80, 1981; Guse et al., Nature 398:70-3, 1999). CD38, via its NAD glycohydrolase activity, also regulates extracellular $NAD^+$ levels, which have been implicated in modulating the regulatory T-cell compartment (Adriouch et al., 14:1284-92, 2012; Chiarugi et al., Nature Reviews 12:741-52, 2012). In addition to signaling via $Ca^{2+}$, CD38 signaling occurs via cross-talk with antigen-receptor complexes on T- and B-cells or other types of receptor complexes, e.g., MHC molecules, involving CD38 in several cellular responses, but also in switching and secretion of IgG1. CD38 is expressed on various malignant cells.

Anti-CD38 antibodies are being developed for the treatment of multiple myeloma and other heme malignancies. The antibodies are either injected or infused via the intravenous (IV) route. The amount of antibody that can be administered via the intravenous route is limited by the physico-chemical properties of the antibody, in particularly by its solubility and stability in a suitable liquid formulation and by the volume of the infusion fluid.

Therefore, there is a need for additional anti-CD38 antibody formulations and pharmaceutical compositions.

SUMMARY OF THE INVENTION

The invention provides a pharmaceutical composition comprising an anti-CD38 antibody and a hyaluronidase.

The invention also provides a pharmaceutical composition comprising an anti-CD38 antibody and a hyaluronidase rHuPH20 having the amino acid sequence of SEQ ID NO: 22.

The invention also provides method of treating a cancer in a subject, comprising administering subcutaneously to the subject in need thereof a pharmaceutical composition comprising an anti-CD38 antibody and a hyaluronidase for a time sufficient to treat the cancer.

The invention also provides a method of treating a CD38-positive hematological malignancy, comprising administering subcutaneously to a subject in need thereof the pharmaceutical composition of the invention for a time sufficient to treat the CD38-positive hematological malignancy.

The invention also provides a method of treating a multiple myeloma, comprising administering subcutaneously to a subject in need thereof the pharmaceutical composition of the invention for a time sufficient to treat the multiple myeloma.

The invention also provides a unit dosage form, comprising
  an anti-CD38 antibody comprising the VH of SEQ ID NO: 4 and the VL of SEQ ID NO: 5 in an amount of from about 1,200 mg to about 5,000 mg;
  a hyaluronidase in an amount of from about 30,000 U to about 45,000 U;
  histidine at a concentration of from about 5 mM to about 15 mM;
  sorbitol at a concentration of from about 100 mM to about 300 mM;
  PS-20 at a concentration of from about 0.01% w/v to about 0.04% w/v; and
  methionine at a concentration of from about 1 mg/mL to about 2 mg/mL, at a pH of about 5.5.

The invention also provides a unit dosage form of claim 74, comprising
  the anti-CD38 antibody comprising the VH of SEQ ID NO: 4 and the VL of SEQ ID NO: 5 in an amount of about 1,800 mg;
  a hyaluronidase in an amount of about 30,000 U;
  histidine at a concentration of about 10 mM;
  sorbitol at a concentration of about 300 mM;
  PS-20 at a concentration of about 0.04% w/v; and
  methionine at a concentration of about 1 mg/mL, at a pH of about 5.5.

The invention also provides a container comprising the unit dosage form of the invention.

The invention also provides a container comprising the pharmaceutical composition of the invention.

DETAILED DESCRIPTION OF THE INVENTION

Figure 1:
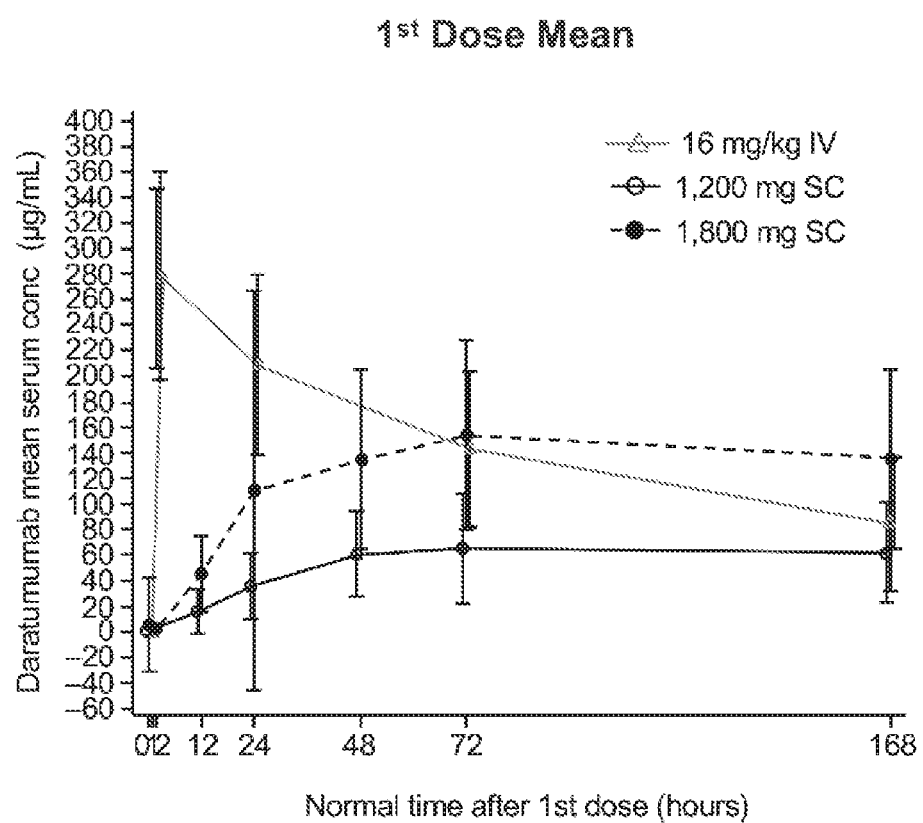
FIG. 1 shows daratumumab mean serum concentration (µg/ml) over time (hours) after administering the $1^{st}$ dose of daratumumab to a patient at the beginning of treatment at 16 mg/kg intravenously (IV), 1,200 mg subcutaneously (SC) or 1,800 mg SC. Vertical bars indicate standard deviation.

"CD38" refers to the human CD38 protein (synonyms: ADP-ribosyl cyclase 1, cADPr hydrolase 1, cyclic ADP-ribose hydrolase 1). Human CD38 has an amino acid sequence shown in GenBank accession number NP_001766 and in SEQ ID NO: 1. It is well known that CD38 is a single pass type II membrane protein with amino acid residues 1-21 representing the cytosolic domain, amino acid residues 22-42 representing the transmembrane domain, and residues 43-300 representing the extracellular domain of CD38.

SEQ ID NO: 1
MANCEFSPVSGDKPCCRLSRRAQLCLGVSILVLILVVVLAVVVPRWRQQ

WSGPGTTKRFPETVLARCVKYTEIHPEMRHVDCQSVWDAFKGAFISKHP

CNITEEDYQPLMKLGTQTVPCNKILLWSRIKDLAHQFTQVQRDMFTLED

TLLGYLADDLTWCGEFNTSKINYQSCPDWRKDCSNNPVSVFWKTVSRRF

AEAACDVVHVMLNGSRSKIFDKNSTFGSVEVHNLQPEKVQTLEAWVIHG

GREDSRDLCQDPTIKELESIISKRNIQFSCKNIYRPDKFLQCVKNPEDS

SCTSEI

"Antibodies" is meant in a broad sense and includes immunoglobulin molecules including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy (H) chains and two light (L) chains inter-connected by disulfide bonds as well as multimers thereof (for example IgM). Each heavy chain is comprised of a heavy chain variable region (VH) and a heavy chain constant region (comprised of domains CH1, hinge CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are "antigen binding sites" in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http://ww-wimgtorg) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

Immunoglobulins may be assigned to five major classes, IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$. Antibody light chains of any vertebrate species can be assigned to one of two clearly distinct types, namely kappa (κ) and lambda (λ), based on the amino acid sequences of their constant domains.

"Antigen-binding fragment" refers to a portion of an immunoglobulin molecule that retains the antigen binding properties of the parental full length antibody. Exemplary antigen-binding fragments are as heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')2, Fd and Fv fragments as well as domain antibodies (dAb) consisting of either one VH domain or one VL domain. VH and VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Monoclonal antibody" refers to an antibody population with single amino acid composition in each heavy and each light chain, except for possible well known alterations such as removal of C-terminal lysine from the antibody heavy chain. Monoclonal antibodies typically bind one antigenic epitope, except that multispecific monoclonal antibodies bind two or more distinct antigens or epitopes. Bispecific monoclonal antibodies bind two distinct antigenic epitopes. Monoclonal antibodies may have heterogeneous glycosylation within the antibody population. Monoclonal antibody may be monospecific or multispecific, or monovalent, bivalent or multivalent. A multispecific antibody, such as a bispecific antibody or a trispecific antibody is included in the term monoclonal antibody.

"Isolated antibody" refers to an antibody or an antigen-binding fragment thereof that is substantially free of other antibodies having different antigenic specificities (e.g., an isolated antibody specifically binding human CD38 is substantially free of antibodies that specifically bind antigens other than human CD38). In case of a bispecific antibody, the bispecific antibody specifically binds two antigens of interest, and is substantially free of antibodies that specifically bind antigens other that the two antigens of interest. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

"Humanized antibodies" refers to antibodies in which the antigen binding sites are derived from non-human species and the variable region frameworks are derived from human immunoglobulin sequences. Humanized antibodies may include intentionally introduced mutations in the framework regions so that the framework may not be an exact copy of expressed human immunoglobulin or germline gene sequences.

"Human antibodies" refers to antibodies having heavy and light chain variable regions in which both the framework and the antigen binding site are derived from sequences of human origin. If the antibody contains a constant region or a portion of the constant region, the constant region also is derived from sequences of human origin.

A human antibody comprises heavy or light chain variable regions that are derived from sequences of human origin if the variable regions of the antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci as described herein. A human antibody typically contains amino acid differences when compared to the human germline or rearranged immunoglobulin sequences due to, for example naturally occurring somatic mutations, intentional introduction of substitutions into the framework or antigen binding site and amino acid changes introduced during cloning and VDJ recombination in non-human animals. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000, or synthetic HCDR3 incorporated into human immunoglobulin gene libraries displayed on phage, for example as described in Shi et al., J Mol Biol 397:385-96, 2010 and Int. Pat. Publ. No. WO2009/085462.

Antibodies in which antigen binding sites are derived from a non-human species are not included in the definition of human antibody.

"Recombinant" includes antibodies and other proteins that are prepared, expressed, created or isolated by recombinant means.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Multispecific" refers to an antibody that specifically binds at least two distinct antigens or two distinct epitopes within the antigens, for example three, four or five distinct antigens or epitopes.

"Bispecific" refers to an antibody that specifically binds two distinct antigens or two distinct epitopes within the same antigen. The bispecific antibody may have cross-reactivity to other related antigens or can bind an epitope that is shared between two or more distinct antigens.

"Variant" refers to a polypeptide or a polynucleotide that differs from a reference polypeptide or a reference polynucleotide by one or more modifications for example, substitutions, insertions or deletions.

"In combination with" means that two or more therapeutics are administered to a subject together in a mixture, concurrently as single agents or sequentially as single agents in any order.

"Pharmaceutical composition" refers to a product that results from combining an anti-CD38 antibody and a hyaluronidase and includes both fixed and non-fixed combinations. Pharmaceutical composition typically includes a pharmaceutically acceptable carrier. "Fixed combinations" refers to a single pharmaceutical composition comprising the anti-CD38 antibody and the hyaluronidase administered simultaneously in the form of a single entity or dosage. "Non-fixed combination" refers to separate pharmaceutical compositions of the anti-CD38 antibody and the hyaluronidase or unit dosage forms administered as separate entities either simultaneously, concurrently or sequentially with no specific intervening time limits, wherein such administration provides effective levels of the two compounds in the body of the subject.

"Pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

"Treat" or "treatment" refers to therapeutic treatment wherein the object is to slow down (lessen) an undesired physiological change or disease, such as the development or spread of tumor or tumor cells, or to provide a beneficial or desired clinical outcome during treatment. Beneficial or desired clinical outcomes include alleviation of symptoms, diminishment of extent of disease, stabilized (i.e., not worsening) state of disease, delay or slowing of disease progression, lack of metastasis, amelioration or palliation of the disease state, and remission (whether partial or total), whether detectable or undetectable. "Treatment" may also mean prolonging survival as compared to expected survival if a subject was not receiving treatment. Those in need of treatment include those subjects already with the undesired physiological change or disease well as those subjects prone to have the physiological change or disease.

"Therapeutically effective amount" refers to an amount effective, at dosages and for periods of time necessary, to achieve the desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics include, for example, improved well-being of the patient, reduction in a tumor burden, arrested or slowed growth of a tumor, and/or absence of metastasis of cancer cells to other locations in the body.

"Inhibits growth" (e.g. referring to tumor cells) refers to a measurable decrease in the tumor cell growth or tumor tissue in vitro or in vivo when contacted with a therapeutic or a combination of therapeutics or drugs, when compared to the growth of the same tumor cells or tumor tissue in the absence of the therapeutic or the combination of therapeutic drugs. Inhibition of growth of a tumor cell or tumor tissue in vitro or in vivo may be at least about 10%, 20%, 30%, 40%, 50%, 60%, 70%, 80%, 90%, 99%, or 100%.

"CD38-positive hematological malignancy" refers to a hematological malignancy characterized by the presence of tumor cells expressing CD38 including leukemias, lymphomas and myeloma. Examples of such CD38-positive hematological malignancies include precursor B-cell lymphoblastic leukemia/lymphoma and B-cell non-Hodgkin's lymphoma, acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma, plasma cell leukemia, post-transplant lymphoproliferative disorder, light chain amyloidosis, Waldenstrom's macroglobulinemia, plasma cell leukemias and anaplastic large-cell lymphoma (ALCL).

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

The following abbreviations are used throughout the disclosure: subcutaneous (SC); intravenous (IV); infusion related reaction (IRR); autologous stem cell transplantation (ASCT); proteasome inhibitor (PI); immunomodulatory drug (IMiD); Nephelometric Turbidity Units (NTU); stringent complete response (sCR); complete response (CR); very good partial response (VGPR); partial response (PR); polysorbate 20 (PS-20); adverse event (AE); progression-free survival (PFS); overall response rate (ORR); overall survival (OS); duration of response (DR); minimal response (MR); stable disease (SD); progressive disease (PD); antibody-dependent cellular cytotoxicity (ADCC), antibody-dependent cellular phagocytosis (ADCP), complement-dependent cytotoxicity (CDC), complementarity determining region (CDR), daratumumab (DARA); heavy chain CDR (HCDR), heavy chain variable region (VH), light chain CDR (LCDR), light chain variable region (VL); patients (pts); International Myeloma Working Group (IMWG); International Staging System (ISS); multiple myeloma (MM); treatment emergent adverse event (TEAE).

Pharmaceutical Compositions

The invention provides a pharmaceutical composition comprising an anti-CD38 antibody and a hyaluronidase.

The pharmaceutical composition is useful for subcutaneous administration of the anti-CD38 antibody to a subject in need of anti-CD38 antibody therapy, such as a subject having a cancer, for example a CD38-positive hematological malignancy. Without wishing to be bound by any particular theory, subcutaneous administration of the anti-CD38 antibody may have reduced infusion related reaction and achieve improved response rates when compared to the intravenous administration of the anti-CD38 antibody.

In some embodiments, the pharmaceutical composition is a fixed combination.

In some embodiments, the pharmaceutical composition is a non-fixed combination.

In some embodiments, the pharmaceutical composition comprises from about 1 mg/mL to about 180 mg/mL of the anti-CD38 antibody.

In some embodiments, the pharmaceutical composition comprises from about 10 mg/mL to about 180 mg/mL of the anti-CD38 antibody.

In some embodiments, the pharmaceutical composition comprises from about 20 mg/mL to about 160 mg/mL of the anti-CD38 antibody.

In some embodiments, the pharmaceutical composition comprises from about 20 mg/mL to about 140 mg/mL of the anti-CD38 antibody.

In some embodiments, the pharmaceutical composition comprises from about 20 mg/mL to about 120 mg/mL of the anti-CD38 antibody.

In some embodiments, the pharmaceutical composition comprises from about 40 mg/mL to about 120 mg/mL of the anti-CD38 antibody.

In some embodiments, the pharmaceutical composition comprises from about 60 mg/mL to about 120 mg/mL of the anti-CD38 antibody.

In some embodiments, the pharmaceutical composition comprises from about 80 mg/mL to about 120 mg/mL of the anti-CD38 antibody.

In some embodiments, the pharmaceutical composition comprises from about 100 mg/mL to about 120 mg/mL of the anti-CD38 antibody.

In some embodiments, the pharmaceutical composition comprises about 1 mg/mL, about 5 mg/mL, about 10 mg/mL, about 15 mg/mL, about 20 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL or about 180 mg/mL of the anti-CD38 antibody.

In some embodiments, the pharmaceutical composition comprises about 20 mg/mL of the anti-CD38 antibody.

In some embodiments, the pharmaceutical composition comprises about 100 mg/mL of the anti-CD38 antibody.

In some embodiments, the pharmaceutical composition comprises about 120 mg/mL of the anti-CD38 antibody.

In some embodiments, the pharmaceutical composition comprises from about 50 U/mL to about 5,000 U/mL of the hyaluronidase.

In some embodiments, the pharmaceutical composition comprises from about 500 U/mL to about 5,000 U/mL of the hyaluronidase.

In some embodiments, the pharmaceutical composition comprises from about 1,000 U/mL to about 5,000 U/mL of the hyaluronidase.

In some embodiments, the pharmaceutical composition comprises from about 2,000 U/mL to about 5,000 U/mL of the hyaluronidase.

In some embodiments, the pharmaceutical composition comprises from about 50 U/mL to about 2,000 U/mL of the hyaluronidase.

In some embodiments, the pharmaceutical composition comprises from about 500 U/mL to about 2,000 U/mL of the hyaluronidase.

In some embodiments, the pharmaceutical composition comprises from about 1,000 U/mL to about 2,000 U/mL of the hyaluronidase.

In some embodiments, the pharmaceutical composition comprises about 500 U/mL, about 600 U/mL, about 700 U/mL, about 800 U/mL, about 900 U/mL, about 1,000 U/mL, about 1,100 U/mL, about 1,200 U/mL, about 1,300 U/mL, about 1,400 U/mL, about 1,500 U/mL, about 1,600 U/mL, about 1,700 U/mL, about 1,800 U/mL, about 1,900 U/mL, about 2,000 U/mL, about 2,100 U/mL, about 2,200 U/mL, about 2,300 U/mL, about 2,400 U/mL, about 2,500 U/mL, about 2,600 U/mL, about 2,700 U/mL, about 2,800 U/mL, about 2,900 U/mL, about 3,000 U/mL, about 3,100 U/mL, about 3,200 U/mL, about 3,300 U/mL, about 3,400 U/mL, about 3,500 U/mL, about 3,600 U/mL, about 3,700 U/mL, about 3,800 U/mL, about 3,900 U/mL, about 4,000 U/mL, about 4,100 U/mL, about 4,200 U/mL, about 4,300 U/mL, about 4,400 U/mL, about 4,500 U/mL, about 4,600 U/mL, about 4,700 U/mL, about 4,800 U/mL, about 4,900 U/mL or about 5,000 U/mL of the hyaluronidase.

In some embodiments, the pharmaceutical composition comprises about 500 U/mL of the hyaluronidase.

In some embodiments, the pharmaceutical composition comprises about 2,000 U/mL of the hyaluronidase.

In some embodiments, the pharmaceutical composition comprises about 5,000 U/mL of the hyaluronidase.

In some embodiments, the pharmaceutical composition comprises from about 1,200 mg to about 5,000 mg of the anti-CD38 antibody.

In some embodiments, the pharmaceutical composition comprises from about 1,200 mg to about 2,400 mg of the anti-CD38 antibody.

In some embodiments, the pharmaceutical composition comprises from about 1,200 mg to about 1,800 mg of the anti-CD38 antibody.

In some embodiments, the pharmaceutical composition comprises about 1,200 mg of the anti-CD38 antibody.

In some embodiments, the pharmaceutical composition comprises about 1,400 mg of the anti-CD38 antibody.

In some embodiments, the pharmaceutical composition comprises about 1,600 mg of the anti-CD38 antibody.

In some embodiments, the pharmaceutical composition comprises about 1,800 mg of the anti-CD38 antibody.

In some embodiments, the pharmaceutical composition comprises about 2,000 mg of the anti-CD38 antibody.

In some embodiments, the pharmaceutical composition comprises about 2,200 mg of the anti-CD38 antibody.

In some embodiments, the pharmaceutical composition comprises about 2,400 mg of the anti-CD38 antibody.

In some embodiments, the pharmaceutical composition comprises about 2,600 mg of the anti-CD38 antibody.

In some embodiments, the pharmaceutical composition comprises about 2,800 mg of the anti-CD38 antibody.

In some embodiments, the pharmaceutical composition comprises about 3,000 mg of the anti-CD38 antibody.

In some embodiments, the pharmaceutical composition comprises about 3,500 mg of the anti-CD38 antibody.

In some embodiments, the pharmaceutical composition comprises about 4,000 mg of the anti-CD38 antibody.

In some embodiments, the pharmaceutical composition comprises about 4,500 mg of the anti-CD38 antibody.

In some embodiments, the pharmaceutical composition comprises about 5,000 mg of the anti-CD38 antibody.

In some embodiments, the pharmaceutical composition comprises from about 750 U to about 75,000 U of the hyaluronidase.

In some embodiments, the pharmaceutical composition comprises from about 7,500 U to about 45,000 U of the hyaluronidase.

In some embodiments, the pharmaceutical composition comprises from about 30,000 U to about 45,000 U of the hyaluronidase.

In some embodiments, the pharmaceutical composition comprises about 7,500 U, about 8,000 U, about 8,500 U, about 9,000 U, about 10,000 U, about 15,000 U, about 20,000 U, about 21,000 U, about 22,000 U, about 23,000 U, about 24,000 U, about 25,000 U, about 26,000 U, about 27,000 U, about 28,000 U, about 29,000 U, about 30,000 U, about 31,000 U, about 32,000 U, about 33,000 U, about 34,000 U, about 35,000 U, about 36,000 U, about 37,000 U, about 38,000 U, about 39,000 U, about 40,000 U, about 41,000 U, about 42,000 U, about 43,000 U, about 44,000 U, about 45,000 U, about 46,000 U, about 47,000 U, about 48,000 U, about 49,000 U, about 50,000 U, about 55,000 U, about 60,000 U, about 65,000 U, about 70,000 U or about 75,000 U of the hyaluronidase.

In some embodiments, the pharmaceutical composition comprises about 5,000 mg of the anti-CD38 antibody and about 30,000 U of the hyaluronidase.

In some embodiments, the pharmaceutical composition comprises about 5,000 mg of the anti-CD38 antibody and about 45,000 U of the hyaluronidase.

In some embodiments, the pharmaceutical composition comprises about 3,000 mg of the anti-CD38 antibody and about 30,000 U of the hyaluronidase.

In some embodiments, the pharmaceutical composition comprises about 3,000 mg of the anti-CD38 antibody and about 45,000 U of the hyaluronidase.

In some embodiments, the pharmaceutical composition comprises about 2,800 mg of the anti-CD38 antibody and about 30,000 U of the hyaluronidase.

In some embodiments, the pharmaceutical composition comprises about 2,800 mg of the anti-CD38 antibody and about 45,000 U of the hyaluronidase.

In some embodiments, the pharmaceutical composition comprises about 2,600 mg of the anti-CD38 antibody and about 30,000 U of the hyaluronidase.

In some embodiments, the pharmaceutical composition comprises about 2,600 mg of the anti-CD38 antibody and about 45,000 U of the hyaluronidase.

In some embodiments, the pharmaceutical composition comprises about 2,400 mg of the anti-CD38 antibody and about 30,000 U of the hyaluronidase.

In some embodiments, the pharmaceutical composition comprises about 2,400 mg of the anti-CD38 antibody and about 45,000 U of the hyaluronidase.

In some embodiments, the pharmaceutical composition comprises about 2,200 mg of the anti-CD38 antibody and about 30,000 U of the hyaluronidase.

In some embodiments, the pharmaceutical composition comprises about 2,200 mg of the anti-CD38 antibody and about 45,000 U of the hyaluronidase.

In some embodiments, the pharmaceutical composition comprises about 2,000 mg of the anti-CD38 antibody and about 30,000 U of the hyaluronidase.

In some embodiments, the pharmaceutical composition comprises about 2,000 mg of the anti-CD38 antibody and about 45,000 U of the hyaluronidase.

In some embodiments, the pharmaceutical composition comprises about 1,800 mg of the anti-CD38 antibody and about 30,000 U of the hyaluronidase.

In some embodiments, the pharmaceutical composition comprises about 1,800 mg of the anti-CD38 antibody and about 45,000 U of the hyaluronidase.

In some embodiments, the pharmaceutical composition comprises about 1,600 mg of the anti-CD38 antibody and about 30,000 U of the hyaluronidase.

In some embodiments, the pharmaceutical composition comprises about 1,600 mg of the anti-CD38 antibody and about 45,000 U of the hyaluronidase.

In some embodiments, the hyaluronidase is rHuPH20 having the amino acid sequence of SEQ ID NO: 22.

rHuPH20 is a recombinant hyaluronidase (HYLENEX® recombinant) and is described in Int. Pat. Publ. No. WO2004/078140.

Hyaluronidase is an enzyme that degrades hyaluronic acid (EC 3.2.1.35) and lowers the viscosity of hyaluronan in the extracellular matrix, thereby increasing tissue permeability.

Enzymatic activity of hyaluronidase, including rHuPH20 can be defined by units per mL (U/mL) or by total enzyme activity in a particular formulation (U).

The standard definition for one unit (U) of enzyme activity is the amount of enzyme that catalyzes the reaction of 1 nmol of substrate per minute.

In some embodiments, the anti-CD38 antibody in the pharmaceutical composition competes for binding to CD38 with an antibody comprising a heavy chain variable region (VH) of SEQ ID NO: 4 and a light chain variable region (VL) of SEQ ID NO: 5.

In some embodiments, the anti-CD38 antibody in the pharmaceutical composition binds at least to the region SKRNIQFSCKNIYR (SEQ ID NO: 2) and the region EKVQTLEAWVIHGG (SEQ ID NO: 3) of human CD38 (SEQ ID NO: 1).

In some embodiments, the anti-CD38 antibody in the pharmaceutical composition comprises a heavy chain complementarity determining region 1 (HCDR1), a HCDR2, a HCDR3, a light chain complementarity determining region 1 (LCDR1), a LCDR2 and a LCDR3 of SEQ ID NOs: 6, 7 and 8, 9, 10 and 11, respectively.

In some embodiments, the anti-CD38 antibody in the pharmaceutical composition comprises a heavy chain variable region (VH) that is 95%, 96%, 97%, 98%, 99% or 100% identical to the amino acid sequence of SEQ ID NO: 4 and a light chain variable region (VL) that is 95%, 96%, 97%, 98%, 99% or 100% identical to the amino acid sequence of SEQ ID NO: 5.

In some embodiments, the anti-CD38 antibody in the pharmaceutical composition comprises the VH of SEQ ID NO: 4 and the VL of SEQ ID NO: 5.

In some embodiments, the anti-CD38 antibody in the pharmaceutical composition comprises a heavy chain of SEQ ID NO: 12 and a light chain of SEQ ID NO: 13.

```
                                        SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVS

AISGSGGGTYYADSVKGRFTISRDNSKNTLYLQMNSLRAEDTAVYFCAK

DKILWFGEPVFDYWGQGTLVTVSS

SEQ ID NO: 5
EIVLTQSPATLSLSPGERATLSCRASQSVSSYLAWYQQKPGQAPRLLIY

DASNRATGIPARFSGSGSGTDFTLTISSLEPEDFAVYYCQQRSNWPPTF

GQGTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVS

AISGSGGGTYYADSVKGRFTISRDNSKNTLYLQMNSLRAEDTAVYFCAK

DKILWFGEPVFDYWGQGTLVTVSSASTKGPSVFPLAPSSKSTSGGTAAL
```

```
                              -continued
GCLVKDYFPEPVTVSWNSGALTSGVHTFPAVLQSSGLYSLSSVVTVPSS

SLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHY

TQKSLSLSPGK

SEQ ID NO: 13
EIVLTQSPATLSLSPGERATLSCRASQSVSSYLAWYQQKPGQAPRLLIY

DASNRATGIPARFSGSGSGTDFTLTISSLEPEDFAVYYCQQRSNWPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Other exemplary anti-CD38 antibodies that may be used in the pharmaceutical compositions and the methods of the invention are:

mAb003 comprising the VH and the VL sequences of SEQ ID NOs: 14 and 15, respectively and described in U.S. Pat. No. 7,829,693. The VH and the VL of mAb003 may be expressed as IgG1/κ;

mAb024 comprising the VH and the VL sequences of SEQ ID NOs: 16 and 17, respectively, described in U.S. Pat. No. 7,829,693. The VH and the VL of mAb024 may be expressed as IgG1/κ;

MOR-202 (MOR-03087) comprising the VH and the VL sequences of SEQ ID NOs: 18 and 19, respectively, described in U.S. Pat. No. 8,088,896. The VH and the VL of MOR-202 may be expressed as IgG1/κ; or Isatuximab; comprising the VH and the VL sequences of SEQ ID NOs: 20 and 21, respectively, described in U.S. Pat. No. 8,153,765. The VH and the VL of Isatuximab may be expressed as IgG1/κ.

```
                                        SEQ ID NO: 14
QVQLVQSGAEVKKPGSSVKVSCKASGGTFSSYAFSWVRQAPGQGLEWMG

RVIPFLGIANSAQKFQGRVTITADKSTSTAYMDLSSLRSEDTAVYYCAR

DDIAALGPFDYWGQGTLVTVSSAS

SEQ ID NO: 15
DIQMTQSPSSLSASVGDRVTITCRASQGISSWLAWYQQKPEKAPKSLIY

AASSLQSGVPSRFSGSGSGTDFTLTISSLQPEDFATYYCQQYNSYPRTF

GQGTKVEIK

SEQ ID NO: 16
EVQLVQSGAEVKKPGESLKISCKGSGYSFSNYWIGWVRQMPGKGLEWMG

IIYPHDSDARYSPSFQGQVTFSADKSISTAYLQWSSLKASDTAMYYCAR

HVGWGSRYWYFDLWGRGTLVTVSS

SEQ ID NO: 17
EIVLTQSPATLSLSPGERATLSCRASQSVSSYLAWYQQKPGQAPGLLIY

DASNRASGIPARFSGSGSGTDFTLTISSLEPEDFAVYYCQQRSNWPLTF

GGGTKVEIK
```

```
                                        SEQ ID NO: 18
QVQLVESGGGLVQPGGSLRLSCAASGFTFSSYYMNWVRQAPGKGLEWVS

GISGDPSNTYYADSVKGRFTISRDNSKNTLYLQMNSLRAEDTAVYYCAR

DLPLVYTGFAYWGQGTLVTVSS

SEQ ID NO: 19
DIELTQPPSVSVAPGQTARISCSGDNLRHYYVYWYQQKPGQAPVLVIYG

DSKRPSGIPERFSGSNSGNTATLTISGTQAEDEADYYCQTYTGGASLVF

GGGTKLTVLGQ

SEQ ID NO 20:
QVQLVQSGAEVAKPGTSVKLSCKASGYTFTDYWMQWVKQRPGQGLEWIG

TIYPGDGDTGYAQKFQGKATLTADKSSKTVYMHLSSLASEDSAVYYCAR

GDYYGSNSLDYWGQGTSVTVSS

SEQ ID NO: 21:
DIVMTQSHLSMSTSLGDPVSITCKASQDVSTVVAWYQQKPGQSPRRLIY

SASYRYIGVPDRFTGSGAGTDFTFTISSVQAEDLAVYYCQQHYSPPYTF

GGGTKLEIK
```

Other exemplary anti-CD38 antibodies that may be used in the pharmaceutical compositions of the invention are those described in Int. Pat. Publ. No. WO05/103083, Intl. Pat. Publ. No. WO06/125640, Intl. Pat. Publ. No. WO07/042309, Intl. Pat. Publ. No. WO08/047242 or Intl. Pat. Publ. No. WO14/178820.

An exemplary anti-CD38 antibody that may be used in the pharmaceutical compositions of the invention is daratumumab. Daratumumab comprises the heavy chain variable region (VH) and the light chain variable region (VL) amino acid sequences shown in SEQ ID NOs: 4 and 5, respectively, the HCDR1, the HCDR2 and the HCDR3 of SEQ ID NOs: 6, 7 and 8, respectively, the LCDR1, the LCDR2 and the LCDR3 of SEQ ID NOs: 9, 10 and 11, respectively, and is of IgG1/κ subtype and described in U.S. Pat. No. 7,829,693. Daratumumab heavy chain amino acid sequence is shown in SEQ ID NO: 12 and light chain amino acid sequence shown in SEQ ID NO: 13.

The invention also provides a pharmaceutical composition comprising an anti-CD38 antibody comprising the VH of SEQ ID NO: 4 and the VL of SEQ ID NO: 5 and a hyaluronidase rHuPH20 of SEQ ID NO: 22, wherein the anti-CD38 antibody concentration in the pharmaceutical composition is about 20 mg/mL.

The invention also provides a pharmaceutical composition comprising an anti-CD38 antibody comprising the HCDR1, the HCDR2 and the HCDR3 of SEQ ID NOs: 6, 7 and 8, respectively, and the LCDR1, the LCDR2 and the LCDR3 of SEQ ID NOs: 9, 10 and 11, respectively and the hyaluronidase rHuPH20 of SEQ ID NO: 22, wherein the anti-CD38 antibody concentration in the pharmaceutical composition is about 20 mg/mL.

The invention also provides a pharmaceutical composition comprising between about 1,200 mg-1,800 mg of the anti-CD38 antibody comprising the VH of SEQ ID NO: 4 and the VL of SEQ ID NO: 5, and between about 30,000 U-45,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,800 mg of the anti-CD38 antibody comprising the VH of SEQ ID NO: 4 and the VL of SEQ ID NO: 5, and about 30,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,800 mg of the anti-CD38 antibody comprising the VH of SEQ ID NO: 4 and the VL of SEQ ID NO: 5, and about 45,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,600 mg of the anti-CD38 antibody comprising the VH of SEQ ID NO: 4 and the VL of SEQ ID NO: 5, and about 30,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,600 mg of the anti-CD38 antibody comprising the VH of SEQ ID NO: 4 and the VL of SEQ ID NO: 5, and about 45,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,200 mg of the anti-CD38 antibody comprising the VH of SEQ ID NO: 4 and the VL of SEQ ID NO: 5, and about 30,000 U of the hyaluronidase rHuPH20 of SEQ ID NO: 22, wherein the anti-CD38 antibody concentration in the pharmaceutical composition is about 20 mg/mL.

The invention also provides a pharmaceutical composition comprising about 1,200 mg of the anti-CD38 antibody comprising the VH of SEQ ID NO: 4 and the VL of SEQ ID NO: 5, and about 45,000 U of the hyaluronidase rHuPH20 of SEQ ID NO: 22, wherein the anti-CD38 antibody concentration in the pharmaceutical composition is about 20 mg/mL.

```
                                        SEQ ID NO: 22
MGVLKFKHIFFRSFVKSSGVSQIVFTFLLIPCCLTLNFRAPPVIPNVPF

LWAWNAPSEFCLGKFDEPLDMSLFSFIGSPRINATGQGVTIFYVDRLGY

YPYIDSITGVTVNGGIPQKISLQDHLDKAKKDITFYMPVDNLGMAVIDW

EEWRPTWARNWKPKDVYKNRSIELVQQQNVQLSLTEATEKAKQEFEKAG

KDFLVETIKLGKLLRPNHLWGYYLFPDCYNHHYKKPGYNGSCFNVEIKR

NDDLSWLWNESTALYPSIYLNTQQSPVAATLYVRNRVREAIRVSKIPDA

KSPLPVFAYTRIVFTDQVLKFLSQDELVYTFGETVALGASGIVIWGTLS

IMRSMKSCLLLDNYMETILNPYIINVTLAAKMCSQVLCQEQGVCIRKNW

NSSDYLHLNPDNFAIQLEKGGKFTVRGKPTLEDLEQFSEKFYCSCYSTL

SCKEKADVKDTDAVDVCIADGVCIDAFLKPPMETEEPQIFYNASPSTLS

ATMFIVSILFLIISSVASL
```

Anti-CD38 antibodies used in the pharmaceutical compositions of the invention, may also be selected de novo from, e.g., a phage display library, where the phage is engineered to express human immunoglobulins or portions thereof such as Fabs, single chain antibodies (scFv), or unpaired or paired antibody variable regions (Knappik et al., J Mol Biol 296:57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from e.g., phage display libraries expressing antibody heavy and light chain variable regions as fusion proteins with bacteriophage pIX coat protein as described in Shi et al., J. Mol. Biol. 397: 385-96, 2010 and Intl. Pat. Publ. No. WO09/085462). The antibody libraries may be screened for binding to human CD38 extracellular domain, the obtained positive clones further characterized, Fabs isolated from the clone lysates, and subsequently cloned as full length antibodies. Such phage display methods for isolating human antibodies are established in the art. See for example: U.S. Pat. Nos. 5,223,409, 5,403,484, 5,571,698, 5,427,908, 5,580,717, 5,969,108, 6,172,197, 5,885,793, 6,521,404, 6,544,731, 6,555,313, 6,582,915, and 6,593,081.

Antibodies may be evaluated for their competition with a reference antibody such as the anti-CD38 antibody comprising the VH of SEQ ID NO: 4 and the VL of SEQ ID NO: 5 for binding to CD38 using known in vitro methods. In an exemplary method, CHO cells recombinantly expressing CD38 may be incubated with unlabeled reference antibody for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of unlabeled reference antibody may be added for about 15 minutes and subsequently biotinylated test antibodies may be added. After washes in PBS/Tween, binding of the test biotinylated antibody may be detected using horseradish peroxidase (HRP)-conjugated streptavidine and the signal detected using standard methods. It is readily apparent that in the competition assays, the reference antibody may be labelled and the test antibody unlabeled. The test antibody competes with the reference antibody when the reference antibody inhibits binding of the test antibody, or the test antibody inhibits binding of the reference antibody by at least 80%, for example 81%, 82%, 83%, 84%, 85%, 86%, 87%, 88%, 89%, 90%, 91%, 92%, 93%, 94%, 95%, 96%, 97%, 98%, 99% or 100%. The epitope of the test antibody may further be defined for example by peptide mapping or hydrogen/deuterium protection assays using known methods, or by crystal structure determination.

Antibodies binding to the region SKRNIQFSCKNIYR (SEQ ID NO: 2) and the region EKVQTLEAWVIHGG (SEQ ID NO: 3) of human CD38 (SEQ ID NO: 1) may be generated for example by immunizing mice with peptides having the amino acid sequences shown in SEQ ID NOs: 2 and 3 using standard methods and those described herein, and characterizing the obtained antibodies for binding to the peptides using for example ELISA or mutagenesis studies.

The invention also provides a pharmaceutical composition comprising an anti-CD38 antibody comprising the HCDR1, the HCDR2, the HCDR3, the LCDR1, the LCDR2, and the LCDR3 sequences of:
  a. the VH of SEQ ID NO: 14 and the VL of SEQ ID NO: 15;
  b. the VH of SEQ ID NO: 16 and the VL of SEQ ID NO: 17;
  c. the VH of SEQ ID NO: 18 and the VL of SEQ ID NO: 19; or
  d. the VH of SEQ ID NO: 20 and the VL of SEQ ID NO: 21, and the hyaluronidase rHuPH20 of SEQ ID NO: 22.

The invention also provides a pharmaceutical composition comprising an anti-CD38 antibody comprising
  a. the VH of SEQ ID NO: 14 and the VL of SEQ ID NO: 15;
  b. the VH of SEQ ID NO: 16 and the VL of SEQ ID NO: 17;
  c. the VH of SEQ ID NO: 18 and the VL of SEQ ID NO: 19; or
  d. the VH of SEQ ID NO: 20 and the VL of SEQ ID NO: 21, and the hyaluronidase rHuPH20 of SEQ ID NO: 22.

The pharmaceutical compositions of the invention further comprise a pharmaceutically acceptable carrier. Exemplary pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof.

Exemplary buffers that may be used are acetic acid, citric acid, formic acid, succinic acid, phosphoric acid, carbonic acid, malic acid, aspartic acid, histidine, boric acid, Tris buffers, HEPPSO and HEPES.

Exemplary antioxidants that may be used are ascorbic acid, methionine, cysteine hydrochloride, sodium bisulfate, sodium metabisulfite, sodium sulfite, lecithin, citric acid, ethylenediamine tetraacetic acid (EDTA), sorbitol and tartaric acid.

Exemplary amino acids that may be used are histidine, isoleucine, methionine, glycine, arginine, lysine, L-leucine, tri-leucine, alanine, glutamic acid, L-threonine, and 2-phenylamine.

Exemplary surfactants that may be used are polysorbates (e.g., polysorbate-20 or polysorbate-80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc).

Exemplary preservatives that may be used are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl and the like), benzalkonium chloride, benzethonium chloride, sodium dehydroacetate and thimerosal, or mixtures thereof.

Exemplary saccharides that may be used are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol or iso-maltulose.

Exemplary salts that may be used are acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenylsubstituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. An exemplary salt is sodium chloride.

The amounts of pharmaceutically acceptable carrier(s) in the pharmaceutical compositions may be determined experimentally based on the activities of the carrier(s) and the desired characteristics of the formulation, such as stability and/or minimal oxidation.

In some embodiments, the pharmaceutical composition comprises acetic acid.

In some embodiments, the pharmaceutical composition comprises acetic acid at a concentration of from about 1 mM to about 50 mM.

In some embodiments, the pharmaceutical composition comprises acetic acid at a concentration of from about 10 mM to about 40 mM.

In some embodiments, the pharmaceutical composition comprises acetic acid at a concentration of about 10 mM, about 15 mM, about 20 mM, about 25 mM, about 30 mM, about 35 mM, about 40 mM, about 45 mM or about 50 mM.

In some embodiments, the pharmaceutical composition comprises acetic acid at a concentration of about 25 mM.

In some embodiments, the pharmaceutical composition comprises sodium chloride (NaCl).

In some embodiments, the pharmaceutical composition comprises NaCl at a concentration of from about 20 mM to about 100 mM.

In some embodiments, the pharmaceutical composition comprises NaCl at a concentration of from about 40 mM to about 80 mM.

In some embodiments, the pharmaceutical composition comprises NaCl at a concentration of about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM or about 100 mM.

In some embodiments, the pharmaceutical composition comprises NaCl at a concentration of about 60 mM.

In some embodiments, the pharmaceutical composition comprises saccharide.

In some embodiments, saccharide is sucrose.

In some embodiments, saccharide is sorbitol.

In some embodiments, saccharide is mannitol.

In some embodiments, the pharmaceutical composition comprises saccharide at a concentration of from about 50 mM to about 500 mM.

In some embodiments, the pharmaceutical composition comprises saccharide at a concentration of from about 50 mM to about 450 mM.

In some embodiments, the pharmaceutical composition comprises saccharide at a concentration of from about 50 mM to about 400 mM.

In some embodiments, the pharmaceutical composition comprises saccharide at a concentration of from about 50 mM to about 350 mM.

In some embodiments, the pharmaceutical composition comprises saccharide at a concentration of from about 100 mM to about 350 mM.

In some embodiments, the pharmaceutical composition comprises saccharide at a concentration of from about 100 mM to about 300 mM.

In some embodiments, the pharmaceutical composition comprises saccharide at a concentration of about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM or about 500 mM.

In some embodiments, the pharmaceutical composition comprises mannitol.

In some embodiments, the pharmaceutical composition comprises mannitol at a concentration of from about 100 mM to about 180 mM.

In some embodiments, the pharmaceutical composition comprises mannitol at a concentration of from about 120 mM to about 160 mM.

In some embodiments, the pharmaceutical composition comprises mannitol at a concentration of about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM or about 180 mM.

In some embodiments, the pharmaceutical composition comprises mannitol at a concentration of about 140 mM.

In some embodiments, the pharmaceutical composition comprises polysorbate.

In some embodiments, the pharmaceutical composition comprises polysorbate-20 (PS-20).

In some embodiments, the pharmaceutical composition comprises polysorbate-20 (PS-20) at a concentration of from about 0.01% w/v to about 0.1% w/v.

In some embodiments, the pharmaceutical composition comprises polysorbate-20 (PS-20) at a concentration of from about 0.01% w/v to about 0.08% w/v.

In some embodiments, the pharmaceutical composition comprises polysorbate-20 (PS-20) at a concentration of from about 0.01% w/v to about 0.04% w/v.

In some embodiments, the pharmaceutical composition comprises polysorbate-20 (PS-20) at a concentration of about 0.01% w/v, 0.02% w/v, 0.03% w/v, 0.04% w/v, 0.05% w/v, 0.06% w/v, 0.07% w/v, 0.08% w/v, 0.09% w/v or 0.1% w/v.

The invention also provides a pharmaceutical composition comprising
  from about 20 mg/mL to about 120 mg/mL of the anti-CD38 antibody comprising the VH of SEQ ID NO: 4 and the VL of SEQ ID NO: 5 in about 25 mM acetic acid, about 60 mM sodium chloride, about 140 mM mannitol and about 0.04% w/v polysorbate-20 (PS-20); at pH about 5.5; and
  about from 30,000 U to about 45,000 U of the hyaluronidase in 10 mM L-Histidine, 130 mM NaCl, 10 mM L-Methionine, 0.02% Polysorbate 80, pH 6.5.

In some embodiments, the hyaluronidase is rHuPH20 (SEQ ID NO: 22).

In some embodiments, the pharmaceutical composition is a non-fixed combination.

The invention also provides a pharmaceutical composition comprising
  about 20 mg/mL of the anti-CD38 antibody comprising the VH of SEQ ID NO: 4 and the VL of SEQ ID NO:

5 in about 25 mM acetic acid, about 60 mM sodium chloride, about 140 mM mannitol and about 0.04% w/v polysorbate-20 (PS-20); at pH about 5.5; and about 30,000 U of the hyaluronidase in 10 mM L-Histidine, 130 mM NaCl, 10 mM L-Methionine, 0.02% Polysorbate 80, pH 6.5.

In some embodiments, the hyaluronidase is rHuPH20 (SEQ ID NO: 22).

In some embodiments, the pharmaceutical composition is a non-fixed combination.

The invention also provides a pharmaceutical composition comprising about 20 mg/mL of the anti-CD38 antibody comprising the VH of SEQ ID NO: 4 and the VL of SEQ ID NO: 5 in about 25 mM acetic acid, about 60 mM sodium chloride, about 140 mM mannitol and about 0.04% w/v polysorbate-20 (PS-20); at pH about 5.5; and about 45,000 U of the hyaluronidase in 10 mM L-Histidine, 130 mM NaCl, 10 mM L-Methionine, 0.02% Polysorbate 80, pH 6.5.

In some embodiments, the hyaluronidase is rHuPH20 (SEQ ID NO: 22).

In some embodiments, the pharmaceutical composition is a non-fixed combination.

In some embodiments, the pharmaceutical composition comprises histidine.

In some embodiments, the pharmaceutical composition comprises histidine at a concentration of from about 1 mM to about 50 mM.

In some embodiments, the pharmaceutical composition comprises histidine at a concentration of from about 5 mM to about 50 mM.

In some embodiments, the pharmaceutical composition comprises histidine at a concentration of from about 5 mM to about 30 mM.

In some embodiments, the pharmaceutical composition comprises histidine at a concentration of from about 5 mM to about 20 mM.

In some embodiments, the pharmaceutical composition comprises histidine at a concentration of from about 5 mM to about 15 mM.

In some embodiments, the pharmaceutical composition comprises histidine at a concentration of from about 5 mM to about 10 mM.

In some embodiments, the pharmaceutical composition comprises histidine at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM or about 50 mM.

In some embodiments, the pharmaceutical composition comprises histidine at a concentration of about 5 mM.

In some embodiments, the pharmaceutical composition comprises histidine at a concentration of about 10 mM.

In some embodiments, the pharmaceutical composition comprises histidine at a concentration of about 15 mM.

In some embodiments, the pharmaceutical composition comprises histidine at a concentration of about 20 mM.

In some embodiments, the pharmaceutical composition comprises sorbitol at a concentration of from about 50 mM to about 500 mM.

In some embodiments, the pharmaceutical composition comprises sorbitol at a concentration of from about 50 mM to about 450 mM.

In some embodiments, the pharmaceutical composition comprises sorbitol at a concentration of from about 50 mM to about 400 mM.

In some embodiments, the pharmaceutical composition comprises sorbitol at a concentration of from about 50 mM to about 350 mM.

In some embodiments, the pharmaceutical composition comprises sorbitol at a concentration of from about 100 mM to about 350 mM.

In some embodiments, the pharmaceutical composition comprises sorbitol at a concentration of from about 100 mM to about 300 mM.

In some embodiments, the pharmaceutical composition comprises sorbitol at a concentration of about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM or about 500 mM.

In some embodiments, the pharmaceutical composition comprises sorbitol at a concentration of about 50 mM.

In some embodiments, the pharmaceutical composition comprises sorbitol at a concentration of about 100 mM.

In some embodiments, the pharmaceutical composition comprises sorbitol at a concentration of about 150 mM.

In some embodiments, the pharmaceutical composition comprises sorbitol at a concentration of about 200 mM.

In some embodiments, the pharmaceutical composition comprises sorbitol at a concentration of about 250 mM.

In some embodiments, the pharmaceutical composition comprises sorbitol at a concentration of about 300 mM.

In some embodiments, the pharmaceutical composition comprises sorbitol at a concentration of about 350 mM.

In some embodiments, the pharmaceutical composition comprises sorbitol at a concentration of about 400 mM.

In some embodiments, the pharmaceutical composition comprises sucrose at a concentration of from about 50 mM to about 500 mM.

In some embodiments, the pharmaceutical composition comprises sucrose at a concentration of from about 50 mM to about 450 mM.

In some embodiments, the pharmaceutical composition comprises sucrose at a concentration of from about 50 mM to about 400 mM.

In some embodiments, the pharmaceutical composition comprises sucrose at a concentration of from about 50 mM to about 350 mM.

In some embodiments, the pharmaceutical composition comprises sucrose at a concentration of from about 100 mM to about 350 mM.

In some embodiments, the pharmaceutical composition comprises sucrose at a concentration of from about 100 mM to about 200 mM.

In some embodiments, the pharmaceutical composition comprises sucrose at a concentration of about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM or about 500 mM.

In some embodiments, the pharmaceutical composition comprises sucrose at a concentration of about 50 mM.

In some embodiments, the pharmaceutical composition comprises sucrose at a concentration of about 100 mM.

In some embodiments, the pharmaceutical composition comprises sucrose at a concentration of about 150 mM.

In some embodiments, the pharmaceutical composition comprises sucrose at a concentration of about 200 mM.

In some embodiments, the pharmaceutical composition comprises sucrose at a concentration of about 250 mM.

In some embodiments, the pharmaceutical composition comprises sucrose at a concentration of about 300 mM.

In some embodiments, the pharmaceutical composition comprises sucrose at a concentration of about 350 mM.

In some embodiments, the pharmaceutical composition comprises sucrose at a concentration of about 400 mM.

In some embodiments, the pharmaceutical composition comprises methionine.

In some embodiments, the pharmaceutical composition comprises methionine at a concentration of from about 0.1 mg/mL to about 5 mg/mL.

In some embodiments, the pharmaceutical composition comprises methionine at a concentration of from about 0.1 mg/mL to about 2.5 mg/mL.

In some embodiments, the pharmaceutical composition comprises methionine at a concentration of from about 1 mg/mL to about 2 mg/mL.

In some embodiments, the pharmaceutical composition comprises methionine at a concentration of about 0.5 mg/mL, about 1 mg/mL, about 1.1 mg/mL, about 1.2 mg/mL, about 1.3 mg/mL, about 1.4 mg/mL, about 1.5 mg/mL, about 1.6 mg/mL, about ½ mg/mL, about 1.8 mg/mL, about 1.9 mg/mL, about 2.0 mg/mL, about 2.1 mg/mL, about 2.2 mg/mL, about ⅔ mg/mL, about 2.4 mg/mL, about 2.5 mg/mL, about 2.6 mg/mL, about 2.7 mg/mL, about 2.8 mg/mL, about 2.9 mg/mL, about 3 mg/mL, about 3.5 mg/mL, about 4 mg/mL, about 4.5 mg/mL or about 5 mg/mL.

In some embodiments, the pharmaceutical composition is at pH 5.0 to 6.0.

In some embodiments, the pharmaceutical composition is at pH 5.3 to 5.8.

In some embodiments, the pharmaceutical composition is at pH 5.5.

In some embodiments, the pharmaceutical composition is at pH 5.6.

The invention also provides a pharmaceutical composition comprising
from about 1 mg/mL to about 180 mg/mL of the anti-CD38 antibody;
from about 50 U/mL to about 5,000 U/mL of the hyaluronidase
from about 5 mM to about 50 mM histidine; and
from about 50 mM to about 400 mM sorbitol.

In some embodiments, the hyaluronidase is rHuPH20.

The invention also provides a pharmaceutical composition comprising
from about 1 mg/mL to about 180 mg/mL of the anti-CD38 antibody;
from about 50 U/mL to about 5,000 U/mL of the hyaluronidase
from about 5 mM to about 50 mM histidine;
from about 50 mM to about 400 mM sorbitol;
from about 0.01% w/v to about 0.1% PS-20; and
from about 0.1 mg/mL to about 2.5 mg/mL methionine.

In some embodiments, the hyaluronidase is rHuPH20.

The invention also provides a pharmaceutical composition comprising
from about 100 mg/mL to about 120 mg/mL of the anti-CD38 antibody;
from about 50 U/mL to about 5,000 U/mL of the hyaluronidase;
about 10 mM histidine; and
from about 100 mM to about 300 mM sorbitol.

In some embodiments, the hyaluronidase is rHuPH20.

In some embodiments, the pharmaceutical composition further comprises from
about 0.01% w/v to about 0.04% w/v PS-20.

In some embodiments, the pharmaceutical composition further comprises from about 1 mg/mL to about 2 mg/mL methionine.

In some embodiments, the pharmaceutical composition further comprises from about 100 mM to about 200 mM sucrose.

In some embodiments, the anti-CD38 antibody comprises
the HCDR1, the HCDR2, the HCDR3, the LCDR1, the LCDR2 and the LCDR3 of SEQ ID NOs: 6, 7, 8, 9, 10 and 11, respectively;
the VH and the VL of SEQ ID NOs: 4 and 5, respectively; and/or
the heavy chain and the light chain of SEQ ID NOs: 12 and 13, respectively.

In some embodiments, the anti-CD38 antibody comprises
the VH and the VL of SEQ ID NOs: 14 and 15, respectively;
the VH and the VL of SEQ ID NOs: 16 and 17, respectively;
the VH and the VL of SEQ ID NOs: 18 and 19, respectively; or
the VH and the VL of SEQ ID NOs: 20 and 21, respectively;

In some embodiments, the hyaluronidase comprises rHuPH20 (SEQ ID NO: 22)

The invention also provides a pharmaceutical composition comprising
from about 1 mg/mL to about 180 mg/mL of the anti-CD38 antibody comprising the VH and the VL of SEQ ID NOs: 4 and 5, respectively;
from about 50 U/mL to about 5,000 U/mL of the hyaluronidase
from about 5 mM to about 50 mM histidine; and
from about 50 mM to about 400 mM sorbitol.

In some embodiments, the hyaluronidase is rHuPH20.

The invention also provides a pharmaceutical composition comprising
from about 1 mg/mL to about 180 mg/mL of the anti-CD38 antibody comprising the VH and the VL of SEQ ID NOs: 4 and 5, respectively;
from about 50 U/mL to about 5,000 U/mL hyaluronidase
from about 5 mM to about 50 mM histidine;
from about 50 mM to about 400 mM sorbitol;
from about 0.01% w/v to about 0.1% PS-20; and from about 0.1 mg/mL to about 2.5 mg/mL methionine.

In some embodiments, the hyaluronidase is rHuPH20.

The invention also provides a pharmaceutical composition comprising
- from about 100 mg/mL to about 120 mg/mL of the anti-CD38 antibody comprising the VH and the VL of SEQ ID NOs: 4 and 5, respectively;
- from about 50 U/mL to about 5,000 U/mL rHuPH20;
- about 10 mM histidine;
- from about 100 mM to about 300 mM sorbitol;
- from about 0.01% w/v to about 0.04% w/v PS-20; and
- from about 1 mg/mL to about 2 mg/mL methionine.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol;
- about 0.04% w/v PS-20; and
- about 2 mg/mL methionine; at pH about 5.5.

The invention also provides a pharmaceutical composition comprising
- about 120 mg/mL of the anti-CD38 antibody comprising the VH and the VL of SEQ ID NOs: 4 and 5, respectively;
- about 2,000 U/mL rHuPH20;
- about 10 mM histidine;
- about 300 mM sorbitol;
- about 0.04% w/v PS-20; and
- about 1 mg/mL methionine; at pH about 5.6.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol; and
- about 2 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol;
- about 0.01% w/v PS-20; and
- about 2 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol;
- about 0.02% w/v PS-20; and
- about 2 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol;
- about 0.06% w/v PS-20; and
- about 2 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 50 U/mL rHuPH20;
- about 10 mM histidine;
- about 300 mM sorbitol;
- about 0.04% w/v PS-20; and
- about 1 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 500 U/mL rHuPH20;
- about 10 mM histidine;
- about 300 mM sorbitol;
- about 0.04% w/v PS-20; and
- about 1 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 2,000 U/mL rHuPH20;
- about 10 mM histidine;
- about 300 mM sorbitol;
- about 0.04% w/v PS-20; and
- about 1 mg/mL methionine; at pH about 5.5.

The invention also provides a pharmaceutical composition comprising
- about 100 mg/mL of the anti-CD38 antibody comprising the VH and the VL of SEQ ID NOs: 4 and 5, respectively;
- about 5,000 U/mL rHuPH20;
- about 10 mM histidine;
- about 300 mM sorbitol;
- about 0.04% w/v PS-20; and
- about 1 mg/mL methionine; at pH about 5.5.

In some embodiments, the pharmaceutical composition is a fixed combination.

The formulations to be used for in vivo administration are generally sterile. Sterility may be readily accomplished, e.g., by filtration through sterile filtration membranes.

The pharmaceutical compositions of the invention may be prepared by known methods. For example, the pharmaceutical compositions may be prepared, e.g., by dissolving, suspending or emulsifying the anti-CD38 antibody in a sterile aqueous medium or an oily medium conventionally used for injections.

Administration

The pharmaceutical compositions of the invention may be administered as a non-fixed combination.

The pharmaceutical compositions of the invention may also be administered as a fixed combination, e.g., as a unit dosage form (or dosage unit form). Fixed combinations may be advantageous for ease of administration and uniformity of dosage.

The invention also provides a unit dosage form, comprising the anti-CD38 antibody comprising the VH of SEQ ID NO: 4 and the VL of SEQ ID NO: 5 in an amount of from about 1,200 mg to about 5,000 mg and rHuPH20 in an amount of from about 30,000 U to about 75,000 U.

The invention also provides a unit dosage form, comprising the anti-CD38 antibody comprising the VH of SEQ ID NO: 4 and the VL of SEQ ID NO: 5 in an amount of from about 1,200 mg to about 4,000 mg and rHuPH20 in an amount of from about 30,000 U to about 75,000 U.

The invention also provides a unit dosage form, comprising the anti-CD38 antibody comprising the VH of SEQ ID NO: 4 and the VL of SEQ ID NO: 5 in an amount of from about 1,200 mg to about 2,400 mg and rHuPH20 in an amount of from about 30,000 U to about 45,000 U.

The invention also provides a unit dosage form, comprising the anti-CD38 antibody comprising the VH of SEQ ID NO: 4 and the VL of SEQ ID NO: 5 in an amount of from about 1,200 mg to about 1,800 mg and rHuPH20 in an amount of from about 30,000 U to about 45,000 U.

The invention also provides a unit dosage form, comprising
  the anti-CD38 antibody comprising the VH of SEQ ID NO: 4 and the VL of SEQ ID NO: 5 in an amount of from about 1,200 mg to about 5,000 mg;
  rHuPH20 in an amount of from about 30,000 U to about 75,000 U;
  histidine at a concentration of from about 5 mM to about 15 mM;
  sorbitol at a concentration of from about 100 mM to about 300 mM;
  PS-20 at a concentration of from about 0.01% w/v to about 0.04% w/v; and
  methionine at a concentration of from about 1 mg/mL to about 2 mg/mL, at a pH of about 5.5.

The invention also provides a unit dosage form, comprising
  the anti-CD38 antibody comprising the VH of SEQ ID NO: 4 and the VL of SEQ ID NO: 5 in an amount of about 1,200 mg to about 2,400 mg;
  rHuPH20 in an amount of from about 30,000 U to about 45,000 U;
  histidine at a concentration of about 10 mM;
  sorbitol at a concentration of about 300 mM;
  PS-20 at a concentration of about 0.04% w/v; and
  methionine at a concentration of from about 1 mg/mL; at a pH of about 5.5.

The invention also provides a unit dosage form, comprising
  the anti-CD38 antibody comprising the VH of SEQ ID NO: 4 and the VL of SEQ ID NO: 5 in an amount of about 1,200 mg to about 1,800 mg;
  rHuPH20 in an amount of from about 30,000 U to about 45,000 U;
  histidine at a concentration of about 10 mM;
  sorbitol at a concentration of about 300 mM;
  PS-20 at a concentration of about 0.04% w/v; and
  methionine at a concentration of from about 1 mg/mL; at a pH of about 5.5.

The invention also provides a unit dosage form, comprising
  the anti-CD38 antibody comprising the VH of SEQ ID NO: 4 and the VL of SEQ ID NO: 5 in an amount of from about 1,200 mg to about 1,800 mg;
  rHuPH20 in an amount of from about 30,000 U to about 45,000 U;
  histidine at a concentration of from about 5 mM to about 15 mM;
  sorbitol at a concentration of from about 100 mM to about 300 mM;
  PS-20 at a concentration of from about 0.01% w/v to about 0.04% w/v; and
  methionine at a concentration of from about 1 mg/mL to about 2 mg/mL, at a pH of about 5.5.

The invention also provides a unit dosage form, comprising
  the anti-CD38 antibody comprising the VH of SEQ ID NO: 4 and the VL of SEQ ID NO: 5 in an amount of about 1,800 mg;
  rHuPH20 in an amount of from about 30,000 U;
  histidine at a concentration of about 10 mM;
  sorbitol at a concentration of about 300 mM;
  PS-20 at a concentration of about 0.04% w/v; and
  methionine at a concentration of from about 1 mg/mL; at a pH of about 5.5.

The invention also provides a unit dosage form, comprising
  the anti-CD38 antibody comprising the VH of SEQ ID NO: 4 and the VL of SEQ ID NO: 5 in an amount of about 1,800 mg;
  rHuPH20 in an amount of from about 45,000 U;
  histidine at a concentration of about 10 mM;
  sorbitol at a concentration of about 300 mM;
  PS-20 at a concentration of about 0.04% w/v; and
  methionine at a concentration of from about 1 mg/mL; at a pH of about 5.5.

The pharmaceutical composition of the invention may be administered in a total volume of about 80 mL, 90 mL, 100 mL, 110 mL or 120 mL.

The pharmaceutical composition of the invention may be administered in a total volume of about 10 mL, 11 mL, 12 mL, 13 mL, 14 mL, 15 mL, 16 mL, 17 mL, 18 mL, 19 mL, 20 mL, 25 mL, 30 mL, 35 mL, 40 mL, 45 mL, 50 mL, 55 mL, 60 mL, 65 mL, 70 mL, 75 mL, 80 mL, 85 mL, 90 mL, 95 mL, 100 mL, 105 mL, 110 mL, 115 mL or 120 mL.

The pharmaceutical composition of the invention may be administered in a total volume of about 10 mL.

The pharmaceutical composition of the invention may be administered in a total volume of about 15 mL.

The pharmaceutical composition of the invention may be administered in a total volume of about 20 mL.

The total volume of administration may be typically smaller for the fixed combinations when compared to the non-fixed combinations.

The invention also provides a container comprising the pharmaceutical composition of the invention.

The invention also provides a container comprising the unit dosage form of the invention.

The container may be a vial, a cartridge, a syringe, a prefilled syringe or a disposable pen.

The administration of the pharmaceutical compositions of the invention may be repeated after one day, two days, three days, four days, five days, six days, one week, two weeks, three weeks, four weeks, five weeks, six weeks, seven weeks, two months, three months, four months, five months, six months or longer. Repeated courses of treatment are also possible, as is chronic administration. The repeated administration may be at the same dose or at a different dose. For example, the pharmaceutical compositions of the invention may be administered once weekly for eight weeks, followed by once in two weeks for 16 weeks, followed by once in four weeks.

The pharmaceutical composition of the invention may be administered subcutaneously.

The pharmaceutical composition of the invention may be administered subcutaneously to the abdominal region.

Subcutaneous administration may be accomplished using a device. The device may be a syringe, a prefilled syringe, an auto-injector, either disposable or reusable, a pen injector, a patch injector, a wearable injector or an ambulatory syringe infusion pump with subcutaneous infusion sets.

For non-fixed combinations, 20 mg/mL anti-CD38 antibody in 25 mM sodium acetate, 60 mM sodium chloride, 140 mM D-mannitol, 0.04% polysorbate 20, pH 5.5 may be mixed with 1 mg/mL (75-150 kU/mL) rHuPH20 in 10 mM L-Histidine, 130 mM NaCl, 10 mM L-Methionine, 0.02% polysorbate-80, pH 6.5 prior to administration of the mixture to a subject.

The pharmaceutical compositions of the invention may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The pharmaceutical composition of the invention may be administered over a time period of between about 10 minutes to about 60 min.

The pharmaceutical composition of the invention may be administered over a time period of about 10 minutes.

The pharmaceutical composition of the invention may be administered over a time period of about 15 minutes.

The pharmaceutical composition of the invention may be administered over a time period of about 20 minutes.

The pharmaceutical composition of the invention may be administered over a time period of about 25 minutes.

The pharmaceutical composition of the invention may be administered over a time period of about 30 minutes.

The pharmaceutical composition of the invention may be administered over a time period of about 30 minutes.

The pharmaceutical composition of the invention may be administered over a time period of about 35 minutes.

The pharmaceutical composition of the invention may be administered over a time period of about 40 minutes.

The pharmaceutical composition of the invention may be administered over a time period of about 45 minutes.

The pharmaceutical composition of the invention may be administered over a time period of about 50 minutes.

The pharmaceutical composition of the invention may be administered over a time period of about 55 minutes.

The pharmaceutical composition of the invention may be administered over a time period of about 60 minutes.

Methods of Treatment

The invention also provides a method of treating a cancer, comprising administering to a subject in need thereof the pharmaceutical composition of the invention for a time sufficient to treat the cancer.

In some embodiments, the cancer is a CD38-positive hematological malignancy.

In some embodiments, the CD38-positive hematological malignancy is multiple myeloma.

In some embodiments, the CD38-positive hematological malignancy is diffuse large B-cell lymphoma (DLBCL).

In some embodiments, the CD38-positive hematological malignancy is non-Hodgkin's lymphoma.

In some embodiments, the CD38-positive hematological malignancy is acute lymphoblastic leukemia (ALL).

In some embodiments, the CD38-positive hematological malignancy is follicular lymphoma (FL).

In some embodiments, the CD38-positive hematological malignancy is Burkitt's lymphoma (BL).

In some embodiments, the CD38-positive hematological malignancy is mantle cell lymphoma (MCL).

In some embodiments, the CD38-positive hematological malignancy is light chain amyloidosis (AL).

In some embodiments, the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In some embodiments, the cancer is a solid tumor.

The invention also provides a method of treating a CD38-positive hematological malignancy, comprising administering to a subject in need thereof a pharmaceutical composition comprising an anti-CD38 antibody and a hyaluronidase subcutaneously for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof a pharmaceutical composition comprising the anti-CD38 antibody comprising the VH of SEQ ID NO: 4 and the VL of SEQ ID NO: 5 and the hyaluronidase rHuPH20 of SEQ ID NO: 22 subcutaneously for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof a pharmaceutical composition comprising between about 1,200 mg-1,800 mg of the anti-CD38 antibody comprising the VH of SEQ ID NO: 4 and the VL of SEQ ID NO: 5, and between about 30,000 U-45,000 U of the hyaluronidase rHuPH20 of SEQ ID NO: 22 for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof a pharmaceutical composition comprising between about 1,200 mg and about 1,800 mg of the anti-CD38 antibody comprising the VH of SEQ ID NO: 4 and the VL of SEQ ID NO: 5, and about 30,000 U of the hyaluronidase rHuPH20 of SEQ ID NO: 22 for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof a pharmaceutical composition comprising between about 1,200 mg and about 1,800 mg of the anti-CD38 antibody comprising the VH of SEQ ID NO: 4 and the VL of SEQ ID NO: 5, and about 45,000 U of the hyaluronidase rHuPH20 of SEQ ID NO: 22 for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof between about 1,600 mg of the anti-CD38 antibody comprising the VH of SEQ ID NO: 4 and the VL of SEQ ID NO: 5, and about 30,000 U of the hyaluronidase rHuPH20 of SEQ ID NO: 22 for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof about 1,600 mg of the anti-CD38 antibody comprising the VH of SEQ ID NO: 4 and the VL of SEQ ID NO: 5, and about 45,000 U of the hyaluronidase rHuPH20 of SEQ ID NO: 22 for a time sufficient to treat the CD38-positive hematological malignancy, wherein the anti-CD38 antibody concentration in the pharmaceutical composition is about 20 mg/mL.

The invention also provides a method of treating a CD38-positive hematological malignancy, comprising administering to a subject in need thereof a pharmaceutical composition comprising the anti-CD38 antibody comprising the VH of SEQ ID NO: 4 and the VL of SEQ ID NO: 5 and the hyaluronidase, wherein the pharmaceutical composition is a non-fixed combination.

The invention also provides a method of treating a CD38-positive hematological malignancy, comprising administering to a subject in need thereof a pharmaceutical composition comprising
- from about 20 mg/mL to about 120 mg/mL of the anti-CD38 antibody comprising the VH of SEQ ID NO: 4 and the VL of SEQ ID NO: 5 in about 25 mM acetic acid, about 60 mM sodium chloride, about 140 mannitol and about 0.04% w/v polysorbate-20 (PS-20); at pH about 5.5; and
- about from 30,000 U to about 45,000 U of the hyaluronidase in 10 mM L-histidine, 130 mM NaCl, 10 mM L-methionine, 0.02% Polysorbate-80, pH 6.5.

In some embodiments, the hyaluronidase is rHuPH20.
In some embodiments, the pharmaceutical composition is a non-fixed combination.

The invention also provides a method of treating a CD38-positive hematological malignancy, comprising administering to a subject in need thereof a pharmaceutical composition comprising
- about 20 mg/mL of the anti-CD38 antibody comprising the VH of SEQ ID NO: 4 and the VL of SEQ ID NO: 5 in about 25 mM acetic acid, about 60 mM sodium chloride, about 140 mannitol and about 0.04% w/v polysorbate-20 (PS-20); at pH about 5.5; and
- about 30,000 U of the hyaluronidase in 10 mM L-histidine, 130 mM NaCl, 10 mM L-methionine, 0.02% Polysorbate-80, pH 6.5.

In some embodiments, the hyaluronidase is rHuPH20.
In some embodiments, the pharmaceutical composition is a non-fixed combination.

The invention also provides a method of treating a CD38-positive hematological malignancy, comprising administering to a subject in need thereof a pharmaceutical composition comprising
- about 20 mg/mL of the anti-CD38 antibody comprising the VH of SEQ ID NO: 4 and the VL of SEQ ID NO: 5 in about 25 mM acetic acid, about 60 mM sodium chloride, about 140 mannitol and about 0.04% w/v polysorbate-20 (PS-20); at pH about 5.5; and
- about 45,000 U of the hyaluronidase in 10 mM L-histidine, 130 mM NaCl, 10 mM L-methionine, 0.02% Polysorbate-80, pH 6.5.

In some embodiments, the hyaluronidase is rHuPH20.
In some embodiments, the pharmaceutical composition is a non-fixed combination.

The invention also provides a method of treating a CD38-positive hematological malignancy, comprising administering to a subject in need thereof a pharmaceutical composition comprising the anti-CD38 antibody comprising the VH of SEQ ID NO: 4 and the VL of SEQ ID NO: 5 and the hyaluronidase, wherein the pharmaceutical composition is a fixed combination.

The invention also provides a method of treating a CD38-positive hematological malignancy, comprising administering to a subject in need thereof a pharmaceutical composition comprising
- from about 1 mg/mL to about 180 mg/mL of the anti-CD38 antibody comprising the VH and the VL of SEQ ID NOs: 4 and 5, respectively;
- from about 50 U/mL to about 5,000 U/mL of the hyaluronidase
- from about 5 mM to about 50 mM histidine; and
- from about 50 mM to about 400 mM sorbitol.

In some embodiments, the hyaluronidase is rHuPH20.

The invention also provides a method of treating a CD38-positive hematological malignancy, comprising administering to a subject in need thereof a pharmaceutical composition comprising
- from about 1 mg/mL to about 180 mg/mL of the anti-CD38 antibody comprising the VH and the VL of SEQ ID NOs: 4 and 5, respectively;
- from about 50 U/mL to about 5,000 U/mL of the hyaluronidase
- from about 5 mM to about 50 mM histidine;
- from about 50 mM to about 400 mM sorbitol;
- from about 0.01% w/v to about 0.1% PS-20; and
- from about 0.1 mg/mL to about 2.5 mg/mL methionine.

In some embodiments, the hyaluronidase is rHuPH20.

The invention also provides a method of treating a CD38-positive hematological malignancy, comprising administering to a subject in need thereof a pharmaceutical composition comprising
- from about 100 mg/mL to about 120 mg/mL of the anti-CD38 antibody comprising the VH and the VL of SEQ ID NOs: 4 and 5, respectively;
- from about 50 U/mL to about 5,000 U/mL of the hyaluronidase;
- about 10 mM histidine;
- from about 100 mM to about 300 mM sorbitol;
- from about 0.01% w/v to about 0.04% w/v PS-20; and
- from about 1 mg/mL to about 2 mg/mL methionine.

In some embodiments, the hyaluronidase is rHuPH20.

The invention also provides a method of treating a CD38-positive hematological malignancy, comprising administering to a subject in need thereof a pharmaceutical composition comprising
- about 100 mg/mL of the anti-CD38 antibody comprising the VH and the VL of SEQ ID NOs: 4 and 5, respectively;
- about 500 U/mL of the hyaluronidase;
- about 10 mM histidine;
- about 300 mM sorbitol;
- about 0.04% w/v PS-20; and
- about 2 mg/mL methionine at pH about 5.5.

In some embodiments, the hyaluronidase is rHuPH20.

The invention also provides a method of treating a CD38-positive hematological malignancy, comprising administering to a subject in need thereof a pharmaceutical composition comprising about 120 mg/mL of the anti-CD38 antibody comprising the VH and the VL of SEQ ID NOs: 4 and 5, respectively;
about 2,000 U/mL rHuPH20;
about 10 mM histidine;
about 300 mM sorbitol;
about 0.04% w/v PS-20; and
about 1 mg/mL methionine; at pH about 5.6.

In some embodiments, the hyaluronidase is rHuPH20.

The anti-CD38 antibodies in the pharmaceutical compositions of the invention may induce killing of CD38-expressing tumor cells by antibody-dependent cell-mediated cytotoxicity (ADCC), antibody-dependent cellular phagocytosis (ADCP), complement dependent cytotoxicity (CDC), apoptosis, or modulation of CD38 enzymatic activity. The anti-CD38 antibodies in the pharmaceutical compositions of the invention may also mediate anti-tumor efficacy by their immunomodulatory effects by inducing CD4$^+$ and CD8$^+$ T cell proliferation, and/or by relieving inhibition of inflammatory responses mediated by myeloid-derived suppressor cells (MDSCs) and regulatory T cells (Tregs).

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD38-expressing cells, occurs as a result of effector cell activity through the secretion of membrane pore-forming proteins and proteases. To assess ADCC activity of an antibody that specifically binds CD38, the antibody may be added to CD38-expressing cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Exemplary effector cells for such assays include peripheral blood mononuclear cells (PBMC) and NK cells. Exemplary target cells include Tregs or MDSCs expressing CD38. In an exemplary assay, target cells are labeled with 20 µCi of $^{51}$Cr for 2 hours and washed extensively. Cell concentration of the target cells may be adjusted to 1×10$^6$ cells/ml, and anti-CD38 antibodies at various concentrations are added. Assays are started by adding target cells at an effector:target cell ratio of 40:1. After incubation for 3 hr at 37° C. assays are stopped by centrifugation, and $^{51}$Cr release from lysed cells are measured in a scintillation counter. Percentage of cellular cytotoxicity may be calculated as % maximal lysis which may be induced by adding 3% perchloric acid to target cells.

"Antibody-dependent cellular phagocytosis" ("ADCP") refers to a mechanism of elimination of antibody-coated target cells by internalization by phagocytic cells, such as macrophages or dendritic cells. ADCP may be evaluated by using Tregs or MDSCs expressing CD38 as target cells engineered to express GFP or other labeled molecule. Effctor:target cell ratio may be for example 4:1. Effector cells may be incubated with target cells for 4 hours with or without anti-CD38 antibody. After incubation, cells may be detached using accutase. Macrophages may be identified with anti-CD11b and anti-CD14 antibodies coupled to a fluorescent label, and percent phagocytosis may be determined based on % GFP fluorescent in the CD11$^+$CD14$^+$ macrophages using standard methods.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes.

The ability of monoclonal antibodies to induce ADCC may be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs may be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the a 1,6-fucosyltrasferase (FUT8) gene (Mori et al., Biotechnol Bioeng 88:901-908, 2004), or coexpression of β-1,4-N-acetylglucosaminyltransferase III and Golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

In some embodiments, the anti-CD38 antibody comprises a substitution in the antibody Fc.

In some embodiments, the anti-CD38 antibody comprises a substitution in the antibody Fc at amino acid positions 256, 290, 298, 312, 356, 330, 333, 334, 360, 378 or 430 (residue numbering according to the EU index).

In some embodiments, the anti-CD38 antibody has a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some embodiments, the anti-CD38 antibody has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the antibody that specifically binds CD38.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Intl. Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS) or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used herein refers to antibodies with fucose content of about 0%-15%.

"Normal fucose" or 'normal fucose content" as used herein refers to antibodies with fucose content of about over 50%, typically about over 60%, 70%, 80% or over 85%.

In the methods described herein, and in some embodiments of each and every one of the numbered embodiments listed below, the anti-CD38 antibody is of IgG1, IgG2, IgG3 or IgG4 isotype.

Antibodies that are substantially identical to the antibody comprising the VH of SEQ ID NO: 4 and the VL of SEQ ID NO: 5 may be used in the methods of the invention. The term "substantially identical" as used herein means that the two antibody VH or VL amino acid sequences being compared are identical or have "insubstantial differences". Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity may be determined for example by pairwise alignment using the default settings of the AlignX module of Vector NTI v.9.0.0 (Invitrogen, Carlsbad, Calif.). The protein sequences of the present invention may be used as a query sequence to perform a search against public or patent databases to, for example, identify related sequences. Exemplary programs used to perform such searches are the XBLAST or BLASTP programs (http_//www_ncbi_nlm/nih_gov), or the GenomeQuest™ (GenomeQuest, Westborough, Mass.) suite using the default settings. Exemplary substitutions that may be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643: 55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis, or modulate CD38 enzymatic activity in vitro using methods described herein.

In some embodiments, the anti-CD38 antibody may bind human CD38 with a range of affinities ($K_D$). In one embodiment according to the invention, and in some embodiments of each and every one of the numbered embodiments listed below, the anti-CD38 antibody binds to CD38 with high affinity, for example, with a $K_D$ equal to or less than about $10^{-7}$ M, such as but not limited to, 1-9.9 (or any range or value therein, such as 1, 2, 3, 4, 5, 6, 7, 8, or 9)×$10^{-8}$ M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One exemplary affinity is equal to or less than 1×$10^{-8}$ M. Another exemplary affinity is equal to or less than 1×$10^{-9}$ M.

In some embodiments, the anti-CD38 antibody is a bispecific antibody. The VL and/or the VH regions of the existing anti-CD38 antibodies or the VL and VH regions identified de novo as described herein may be engineered into bispecific full length antibodies. Such bispecific antibodies may be made by modulating the CH3 interactions between the monospecific antibody heavy chains to form bispecific antibodies using technologies such as those described in U.S. Pat. No. 7,695,936; Intl. Pat. Publ. No. WO04/111233; U.S. Pat. Publ. No. US2010/0015133; U.S. Pat. Publ. No. US2007/0287170; Intl. Pat. Publ. No. WO2008/119353; U.S. Pat. Publ. No. US2009/0182127; U.S. Pat. Publ. No. US2010/0286374; U.S. Pat. Publ. No. US2011/0123532; Intl. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention may be incorporated are for example Dual Variable Domain Immunoglobulins (Inlt. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441).

For example, bispecific antibodies may be generated in vitro in a cell-free environment by introducing asymmetrical mutations in the CH3 regions of two monospecific homodimeric antibodies and forming the bispecific heterodimeric antibody from two parental monospecific homodimeric antibodies in reducing conditions to allow disulfide bond isomerization according to methods described in Intl. Pat.

Publ. No. WO2011/131746. In the methods, the first monospecific bivalent antibody (e.g., anti-CD38 antibody) and the second monospecific bivalent antibody are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

Exemplary CH3 mutations that may be used in a first heavy chain and in a second heavy chain of the bispecific antibody are K409R and/or F405L.

The methods of the invention may be used to treat an animal patient belonging to any classification. Examples of such animals include mammals such as humans, rodents, dogs, cats and farm animals.

Combination Therapies

The pharmaceutical compositions of the invention may be administered in combination with a second therapeutic agent, or combinations thereof.

The second therapeutic agent may be melphalan, mechlorethamine, thioepa, chlorambucil, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin, thalidomide or a thalidomide analog, lenalidomide or CC4047, a proteasome inhibitor, such as bortezomib or *vinca* alkaloid, such as vincristine or an anthracycline, such as doxorubicin.

In some embodiments, the second therapeutic agent is a proteasome inhibitor.

In some embodiments, the proteasome inhibitor is bortezomib, carfilzomib or ixazomib.

In some embodiments, the second therapeutic agent is an alkylating agent.

In some embodiments, the alkylating agent is busulfan, cyclophosphamide, bendamustine, chlorambucli, carboplatin, cisplatin, temozolomide, melphalan, busulfan, bendamustine, carmustine, lomustine, dacarbazine, oxaliplatin, ifosfamide, mechlorethamine, thiotepa, trabectedin or streptozocin.

In some embodiments, the second therapeutic agent is a glutamic acid derivative.

In some embodiments, the glutamic acid derivative is Revlimid® (lenalidomide), thalidomide or Pomalyst® (pomalidomide).

In some embodiments, the subject is further administered a corticosteroid.

In some embodiments, the corticosteroid is dexamethasone or predisone.

The second therapeutic agent or combinations thereof are typically administered at dosages recommended for the agent.

The pharmaceutical composition of the invention may be administered simultaneously or sequentially with the second thereapeutic agent or combinations thereof.

While having described the invention in general terms, the embodiments of the invention will be further disclosed in the following examples that should not be construed as limiting the scope of the claims.

Example 1. Subcutaneous Delivery of 2% Human Immunoglobulin G (IgG) with Recombinant Human Hyaluronidase PH20 (rHuPH20) in the Miniature Swine Model Summary The miniature pig is a preclinical model that is suitable for evaluating subcutaneous (SC) administration conditions of biotherapeutics due to its anatomical similarity to human skin and clinical translatability (Mahj et al., Exp Toxicol Path 57: 341-5, 2006). The objective of this study was to assess and evaluate conditions for a 100 mL administration of a 20 mg/mL human IgG solution containing 200, 500, or 800 U/mL of rHuPH20 at two different flow rates (2 and 4 mL/min). Endpoints included quantitative infusion pressure measurements as well as qualitative assessments of the local infusion site, such as swelling size and firmness.

Yucatan miniature pigs were subcutaneously infused with 100 mL of a solution containing 20 mg/mL immunoglobulin G (IgG) with 200, 500, or 800 U/mL of rHuPH20 at a flow rate of 2 or 4 mL/min. Real-time in-line pressures were measured during infusions. Following the completion of infusions, local infusion sites were measured for visible swelling volume and area if present, and qualitative scoring of the infusion site for presence and severity of erythema, size and firmness of the swelling/bleb, and gross observations. Infusion pressures were low overall and ranged from ~40 to 60 mmHg (~1 PSI) for both flow rates.

There were no statistical differences in pressure between the various concentrations of rHuPH20 and the two different flow rates, with overall pressure being slightly lower at the 2 mL/min flow rate as expected.

The unexpected finding was the number of infusions (10 of 12) that had visible and measurable swelling at the infusion site for the lower 2 mL/min flow rate. This observation was observed at all three concentrations of rHuPH20. In contrast, only 3 of 12 infusions at the higher 4 mL/min flow rate resulted in visible and measurable local swelling. Again this was observed at each concentration of rHuPH20.

In all cases where local swelling was visible, the swelling subsided within an hour. Additionally, local swelling at the infusion sites was generally soft to the touch and not indurated, as indicated by the swelling/induration index (mean score <2). The prevalence of erythema was more frequent with infusions at the 2 mL/min flow rate; however, overall the severity of the erythema was mild and completely subsided by the following day. No other gross observations of the infusion sites were noted in the study.

Three different concentrations of rHuPH20 (200, 500, or 800 U/mL) were evaluated in this study, with no statistical difference between the concentrations based on the endpoints of the study. Overall, the higher 4 mL/min flow rate resulted in lower frequency of erythema, visible swelling, and local infusion site firmness than the 2 mL/min flow rate.

Test Articles and Methods

Test Articles

Materials in Formulation Buffer:
  25 mM sodium acetate (Spectrum; PN#S0104; Lot#1DI0271)
  60 mM sodium chloride (Spectrum; PN#S0155; Lot#1CE0421)

140 mM D-mannitol (Spectrum; PN#MA165; Lot#1EB0316)

0.04% polysorbate 20 (JT Baker; PN#4116-04; Lot#0000017659)

pH 5.5 (glacial acetic acid to pH; Fisher Scientific; PN#A491-212; Lot#080972)

Materials in Drug Substance:

Human Gamma Globulin (BioMed Supply; PN#HGG-1005; Lot#BMS31309013)

rHuPH20 [(Manufactured by Cook Pharmica for Halozyme; Halozyme Lot#462-021B (revialed, Cook Lot#104-001-HSTFIL-9054)]

Formulation 20 mg/mL IgG was co-mixed with 200, 500, or 800 U/mL of rHuPH20 4 days prior to study onset. The solutions were aliquoted into individual glass bottles, sealed with a stopper, and crimp capped. All solutions were stored at 2-8° C. until start of study, but were allowed to acclimate to room temperature prior to infusions. Additionally, a sample was taken from each formulation for rHuPH20 enzymatic activity testing. Results of the enzymatic activity assay confirmed that all dosing solutions were within 10% of the target concentration (data not shown).

Animal Description

Species: Pig (Sus scrofa domestica)
Strain: Yucatan Miniature
Sex: Female
Age: >3 months
Weight: ~12 kg
Quantity: 12
Source: S&S Farms (Ramona, Calif.)

Husbandry

Animals were housed in steel pens with automatic water provided ad libitum. Animals were fed twice daily (AM and PM), except on study day (PM only). Animal body weights were taken and recorded from day of delivery to one day post-completion of the study to assess animal health. All animals maintained body weights during this period (data not shown). The room environment was set to maintain a temperature of ~17-27° C. and a relative humidity of 40-70%, with a 12 hour light/12 hour dark time cycle. Animals were allowed to acclimate to the facility for 7 days prior to study onset.

Test Materials

High pressure syringe pumps (KD Scientific; Holliston, Mass.)
23 ga×¾ inch winged infusion needle set with 12 inch tubing (Terumo Medical Corporation; Somerset, N.J.)
140-cc Luer-lock syringe (Covidien; Mansfield, Mass.)
Extension set 7 inch (B/Braun; Bethlehem, Pa.)
PowerLab 4/30 (AD Instruments; Colorado Springs, Colo.)
Deltran-1 disposable pressure transducer (Utah Medical Products; Midvale, Utah)
Digital caliper (Preisser Messtechnik; Gammertingen, Germany)
Isoflurane (Minrad International Company, Orchard Park, N.Y.)
Isoflurane vaporizer (VetEquip; Pleasanton, Calif.)

Experimental Design

The experimental design is summarized in the Description of Cohorts (Table 1) and Description of Infusions per Animal (Table 2). In brief, 100 mL of a solution containing 20 mg/mL IgG co-mixed with 200, 500, or 800 U/mL of rHuPH20 was administered into the abdominal region of anesthetized Yucatan mini-pigs at a flow rate of 2 or 4 mL/min. The endpoints of the study included infusion pressure measurements using an in-line pressure transducer, local post-infusion swelling (bleb) volume and area (if possible), and qualitative assessment of the infusion site, including photographs.

TABLE 1

| Cohort | Test Article | Flow Rate (mL/min) |
|---|---|---|
| 1 | IgG + 200 U/mL rHuPH20 | 2 mL/min |
| 2 | IgG + 500 U/mL rHuPH20 | |
| 3 | IgG + 800 U/mL rHuPH20 | |
| 4 | IgG + 200 U/mL rHuPH20 | 4 mL/min |
| 5 | IgG + 500 U/mL rHuPH20 | |
| 6 | IgG + 800 U/mL rHuPH20 | |

TABLE 2

| Animal ID | Flow rate (mL/min) | Left side infusion | Right side infusion |
|---|---|---|---|
| 1 | 2 | IgG + 200 U/mL rHuPH20 | IgG + 500 U/mL rHuPH20 |
| 2 | | IgG + 200 U/mL rHuPH20 | IgG + 800 U/mL rHuPH20 |
| 3 | | IgG + 500 U/mL rHuPH20 | IgG + 200 U/mL rHuPH20 |
| 4 | | IgG + 500 U/mL rHuPH20 | IgG + 800 U/mL rHuPH20 |
| 5 | | IgG + 800 U/mL rHuPH20 | IgG + 200 U/mL rHuPH20 |
| 6 | | IgG + 800 U/mL rHuPH20 | IgG + 500 U/mL rHuPH20 |
| 7 | 4 | IgG + 200 U/mL rHuPH20 | IgG + 500 U/mL rHuPH20 |
| 8 | | IgG + 200 U/mL rHuPH20 | IgG + 800 U/mL rHuPH20 |
| 9 | | IgG + 500 U/mL rHuPH20 | IgG + 200 U/mL rHuPH20 |
| 10 | | IgG + 500 U/mL rHuPH20 | IgG + 800 U/mL rHuPH20 |
| 11 | | IgG + 800 U/mL rHuPH20 | IgG + 200 U/mL rHuPH20 |
| 12 | | IgG + 800 U/mL rHuPH20 | IgG + 500 U/mL rHuPH20 | n = 4 infusions per cohort per flow rate
Each animal received 2 different simultaneous infusions (one on each contra-lateral site)
rHuPH20 concentrations: 200 U/mL = 20,000 total U; 500 U/mL = 50,000 total U; 800 U/mL = 80,000 total U
Infusion volume 100 mL
Endpoints:
In-line (infusion) pressure
Measurement of swelling/bleb volume and area
Qualitative assessment of erythema and induration including photographs Study Procedure Prior to start of study, animals were assessed for general health and body weights were collected. On the day of study, animals were anesthetized with isoflurane gas and placed in dorsal recumbence on a heated surgical table, and were maintained under isoflurane gas for the entire duration of the procedure. The abdominal region was cleaned with isopropanol and wiped dry with clean gauze. Infusion sites were located on the left and right abdominal regions, ~3-4 cm towards the midline starting from the cranial end of the inguinal fold and then ~6 cm cranial. The infusion sites were marked with a permanent marker and then photographed. Test articles were acclimated to room temperature prior to infusions. Test articles were drawn into a 140 cc syringe (>100 mL to account for volume needed to prime the line). A pressure transducer was attached to the syringe. A line extension set with an attached 23 ga×¾ inch winged infusion needle was then attached to the transducer. The infusion hardware was then primed to the needle tip. The syringe was loaded into the syringe pump. This process was done in duplicate, with each syringe containing a different test article. The needles were placed subcutaneously into the marked left and right abdominal infusion sites of the animal. The in-line pressure transducer was zeroed. In-line pressure recordings were started and then the two syringe pumps were started simultaneously to infuse 100 mL of test articles at a flow rate of 2 or 4 mL/min. Upon completion of infusions, in-line pressure data collection were stopped, needles removed, and the needle insertion hole sealed with VetBond liquid adhesive to prevent any leakage. Local infusion site swelling/bleb area and volume were measured using a digital caliper. Local infusion sites were also qualitatively assessed for appearance (erythema), swelling/bleb size, and firmness (induration) using a 5 point scoring system (Table 3, Table 4, and Table 5, respectively). Finally, photographs were taken of the infusion sites.

TABLE 3

| Scale | Description |
|---|---|
| 0 | No erythema |
| 1 | Very slight erythema (barely perceptible) |
| 2 | Well defined erythema |
| 3 | Moderate to severe erythema |
| 4 | Severe erythema (beet redness) to slight eschar formation |

TABLE 4

| Scale | Description |
|---|---|
| 0 | No swelling |
| 1 | Very slight swelling |
| 2 | Slight swelling |
| 3 | Moderate swelling |
| 4 | Severe swelling |

TABLE 5

| Scale | Description |
|---|---|
| 0 | No perceptible difference in firmness after injection |
| 1 | Very slightly firm (barely perceptible) |
| 2 | Mildly firm |
| 3 | Moderately firm |
| 4 | Very firm |

Calculations and Statistical Methods
Assessment of Infusion Pressure:

Infusion pressures, as measured via an in-line transducer, were recorded using LabChart 7, and the mean pressure over the entire infusion period was calculated.
Assessment of Local Swelling Volume and Area:

Volume and area of post-infusion swelling were measured using a digital caliper and manually recorded. Measurements were recorded as length, width, and height. The formula for an ellipsoid was used to calculate volume. Volume=$4/3\pi ABC$, where A=radius of length, B=radius of width, C=radius of height. A simple formula of length×width was used to calculate the area.
Assessment of Local Infusion Sites:

Local infusion sites were independently assessed by three separate evaluators following the completion of the infusion. Each evaluator assessed the skin at each infusion site for the presence of erythema, size of local swelling, and firmness. A score on a 0 to 4 grading scale was used to evaluate the three areas of assessment, with a score of 0 representing no effect and 4 being severe. Additionally, erythema and swelling scores were used to calculate a primary irritation index (PII) using the formula PII=mean [($\Sigma$ of erythema grade+$\Sigma$ of swelling grade)÷2]. Furthermore, the swelling and firmness scores were used to calculate a swelling/induration index (SII) using the formula SII=mean [($\Sigma$ of swelling grade+$\Sigma$ of hardness grade)÷2]. A SII score of ≤2 was not considered to be indurated.

Statistical Analyses:

Statistical comparisons between cohorts were performed using an one-way analysis of variance (ANOVA) with a Tukey's multiple comparisons test for continuous variables, and a nonparameteric Krusal-Wallis test with a Dunn's multiple comparisons test for categorical variables. Statistical significance was determined to be $p<0.05$.

Results
Assessment of Infusion Pressure:

100 mL of 20 mg/mL IgG co-mixed with 200, 500, or 800 U/mL of rHuPH20 was administered into the abdominal region of Yucatan mini-pigs at a flow rate of 2 or 4 mL/min. Infusions at a flow rate of 2 mL/min resulted in mean infusion pressures of 40.5±0.1, 40.0±0.1, and 37.1±0.1 mmHg±SEM for IgG co-mixed with 200, 500, and 800 U/mL of rHuPH20, respectively. Infusions at a flow rate of 4 mL/min resulted in mean pressures of 49.9±0.1, 55.5±0.1, and 61.9±0.2 mmHg±SEM for IgG co-mixed with 200, 500, and 800 U/mL of rHuPH20, respectively. The infusion pressures were not statistically different between the various concentrations of rHuPH20 for each flow rate and were not statistically different between the two flow rates.

Assessment of Local Swelling Volume and Area:

After completion of each infusion, the local infusion site swelling was marked if visible and measured using a digital caliper. For infusions at a flow rate of 2 mL/min resulted in a mean swelling volume of 36.6±14.4, 19.5±6.5, and 31.4±6.0 cm3±SEM for IgG co-mixed with 200, 500, and 800 U/mL of rHuPH20, respectively, of which 10 of 12 infusions were visible and measurable. On the contrary, the swelling volume was only detected in 3 of 12 infusions at a flow rate of 4 mL/min, one at each rHuPH20 concentration. The local swelling volumes were not statistically different between the various concentrations of rHuPH20 for each flow rate and were not statistically different between the two flow rates.

In addition to volume calculations, the local area of post-infusion visible swelling was measured. For infusions at a flow rate of 2 mL/min resulted in a mean swelling area of 78.2±26.4, 59.7±20.0, and 94.9±9.7 cm2±SEM for IgG co-mixed with 200, 500, and 800 U/mL of rHuPH20, respectively. For infusions at a flow rate of 4 mL/min resulted in measurable swelling areas in only 3 of 12 infusions, one at each rHuPH20 concentration. The local swelling areas were not statistically different between the various concentrations of rHuPH20 for each flow rate and were not statistically different between the two flow rates.

Assessment of Local Infusion Sites:

Upon completion of infusions, the local infusion sites were qualitatively scored, by three separate evaluators, for presence and severity of erythema, visible size of swelling, physical firmness of the skin, primary irritation index (PII) which incorporates the erythema and swelling scores, and swelling/induration index (SII) which incorporates the swelling and firmness scores to determine if induration was present.

The presence and severity of erythema was evaluated. For infusions at a flow rate of 2 mL/min resulted in a mean erythema score of (±SEM) of 0.8±0.2, 0.4±0.1, and 1.0±0.3 for IgG commixed with 200, 500, and 800 U/mL of rHuPH20, respectively. Infusions at a flow rate of 4 mL/min resulted in a mean erythema score (±SEM) of 0.3±0.1, 0.3±0.1. and 0.2±0.1 for IgG co-mixed with 200, 500, and 800 U/mL of rHuPH20, respectively. The local erythema scores were not statistically different between the various concentrations of rHuPH20 for each flow rate and were not statistically different between the two flow rates. The size of visible local swelling was evaluated, and for infusions at a flow rate of 2 mL/min resulted in a mean swelling score (±SEM) of 1.9±0.4, 1.4±0.3, and 2.0±0.2 for IgG co-mixed with 200, 500, and 800 U/mL of rHuPH20, respectively. Infusions at a flow rate of 4 mL/min had fewer visible swelling with a mean erythema score (±SEM) of 0.6±0.3, 0.9±0.4, and 0.9±0.4 for IgG co-mixed with 200, 500, and 800 U/mL of rHuPH20, respectively. The local swelling scores were not statistically different between the various concentrations of rHuPH20 for each flow rate and was not statistically different between the two flow rates, except for IgG+800 U/mL of rHuPH20 at 2 mL/min flow rate versus IgG+200 U/mL of rHuPH20 at 4 mL/min flow rate (p<0.05). The physical firmness of the skin at the local infusion site was evaluated, and for infusions at a flow rate of 2 mL/min resulted in a mean firmness score (±SEM) of 1.5±0.3, 1.0±0.2, and 1.4±0.2 for IgG co-mixed with 200, 500, and 800 U/mL of rHuPH20, respectively. Infusions at a flow rate of 4 mL/min had less local infusion site firmness with a mean firmness score (±SEM) of 0.5±0.3, 0.7±0.2, and 0.7±0.3 for IgG co-mixed with 200, 500, and 800 U/mL of rHuPH20, respectively. The local infusion site firmness scores were not statistically different between the various concentrations of rHuPH20 for each flow rate and were not statistically different between the two flow rates. The primary irritation index was calculated based on the erythema and swelling scores. Infusions at 2 mL/min had a mean PII score (±SEM) of 1.4±0.3, 0.9±0.2, and 1.5±0.2 for IgG co-mixed with 200, 500, and 800 U/mL of rHuPH20, respectively. Infusions at a flow rate of 4 mL/min had lower PII scores with a mean score (±SEM) of 0.4±0.2, 0.6±0.3, and 0.5±0.3 for IgG co-mixed with 200, 500, and 800 U/mL of rHuPH20, respectively. The PII scores were not statistically different between the various concentrations of rHuPH20 for each flow rate and was not statistically different between the two flow rates, except for IgG+800 U/mL of rHuPH20 at 2 mL/min flow rate versus IgG+200 U/mL of rHuPH20 at 4 mL/min flow rate (p<0.05). The swelling/induration index was calculated based on the swelling and firmness scores. Infusions at 2 mL/min had a mean SII score (±SEM) of 1.7±0.3, 1.2±0.2, and 1.7±0.2 for IgG co-mixed with 200, 500, and 800 U/mL of rHuPH20, respectively. Infusions at a flow rate of 4 mL/min had lower SII scores with a mean score of 0.6±0.3, 0.8±0.3, and 0.8±0.3 (±SEM) for IgG co-mixed with 200, 500, and 800 U/mL of rHuPH20, respectively. The SII scores were not statistically different between the various concentrations of rHuPH20 for each flow rate and was not statistically different between the two flow rates. Based on the mean SII values (score of ≤2), the local infusions sites were considered not to be indurated. Lastly, photographs were taken prior to and after completion of each infusion.

Example 2. An Open-Label, Multicenter, Dose Escalation Phase 1b Study to Assess the Safety and Pharmacokinetics of Subcutaneous Delivery of Daratumumab with the Addition of Recombinant Human Hyaluronidase (rHuPH20) for the Treatment of Subjects with Relapsed or Refractory Multiple Myeloma (PAVO)

The purpose of the study is to evaluate the safety, pharmacokinetics and antitumor activity of subcutaneous (SC) or intravenous (IV) delivery of daratumumab to participants with relapsed or refractory multiple myeloma. This is an open-label multicenter, 2-part, Phase 1b dose escalation/expansion study to evaluate the safety, pharmacokinetics and antitumor activity of SC or IV delivery of daratumumab to participant with relapsed or refractory multiple myeloma. Up to approximately 48 participants in part 1 and 80 participants in part 2 will be enrolled. The Part 1 dose escalation phase is designed to determine the recommended Phase 2 dose (RP2D) based on safety and pharmacokinetic (PK) data of daratumumab. Each part of the study will have 3 phases: a Screening Phase, an open label treatment phase and a post-treatment phase (from the final dose of study drug until post-treatment week 8). In Part 1, participants will be assigned to sequential cohorts of approximately 8 participants each cohort. Participants will be dosed with DARA PH20 (Daratumumab with the Addition of Recombinant Human Hyaluronidase [rHuPH20]) by SC infusion once weekly in Cycles 1 (each cycle 28 days) and 2, every 2 weeks in Cycles 3-6, and every 4 weeks in subsequent cycles of each cohort. After the last participant in each cohort completes Cycle 3 day 1, the Safety Evaluation Team (SET) will evaluate the safety and pharmacokinetic data according to protocol-defined criteria and make the decision whether to escalate the dose in a new cohort. The SET will review all safety and PK data from Part 1 to determine the RP2D before initiation of Part 2. In Part 2, participants will be randomized 1:1 to receive recommended Phase 2 dose of DARA PH20 or IV delivery of 1,200 mg daratumumab. Safety, pharmacokinetics, and antitumor activity of SC and IV delivery of daratumumab will be evaluated. Participant's safety will be monitored throughout the study.

Primary Outcome Measures:

Serum Trough Concentrations (Ctrough) of Daratumumab (Time Frame: Up to part 2 cycle 3 (each cycle 28 days) Day 1). Ctrough: minimum serum concentration after dose administration, and before administration of a subsequent dose.

Part 1 and 2: Number of Participants with Adverse Events (AEs) and Serious AEs (Time Frame: Screening up to follow-up (30 days after last dose administration)

An adverse event (AE) is any untoward medical occurrence in a participant who received study drug without regard to possibility of causal relationship. A serious adverse event (SAE) is an AE resulting in any of the following outcomes or deemed significant for any other reason: death; initial or prolonged inpatient hospitalization; life-threatening experience (immediate risk of dying); persistent or significant disability/incapacity; congenital anomaly.

Secondary Outcome Measures:

Part 1 and 2: Serum Concentration of Daratumumab and Recombinant Human Hyaluronidase (rHuPH20) (Plasma) Antibodies (Time Frame: Approximately 2 years). Serum levels of antibodies to daratumumab and rHuPH20 for evaluation of potential immunogenicity.

Part 1 and 2: Percentage of Participants with Complete Response (CR) (Time Frame: Approximately 2 years). CR is defined as the proportion of Participants achieving CR (including sCR) according to the International Myeloma Working Group (IMWG) criteria.

Part 1 and 2: Percentage of Participants With Overall Response Rate (ORR) (Time Frame: Approximately 2 years). Overall response rate is defined as the percentage of participants who achieve complete response or partial response according to the International Myeloma Working Group (IMWG) criteria, during or after study treatment.

Part 1 and 2: Duration of Response (DR) (Time Frame: Approximately 2 years). The DR is time from date of initial documentation of response (CR or PR) to date of first documented PD, as defined by IMWG criteria.

Part 1 and 2: Time to Response (Time Frame: Approximately 2 years). Time to response is defined as the time from the date of first dose of study treatment to the date of the first documentation of observed response (CR or PR).

Table 6 shows the study design. Table 7 shows the interventions.

TABLE 6

| Arm Number or Name | Type | Description |
|---|---|---|
| Part 1: Cohort 1 | Experimental | Participants will receive DARA PH20, 1,200 mg (daratumumab 1,200 milligram (mg) with Recombinant Human Hyaluronidase [rHuPH20] 30,000 U) by Subcutaneous (SC) infusion once weekly in Cycles 1 (each cycle is 28 days) and 2, every 2 weeks in Cycles 3-6, and then every 4 weeks in subsequent cycles until disease progression. |
| Part 1: Cohort 2 | Experimental | Participants will receive DARA PH20, 1,800 mg (daratumumab 1,800 milligram (mg) with Recombinant Human Hyaluronidase [rHuPH20] 45,000 U) by SC infusion once weekly in Cycles 1 and 2, every 2 weeks in Cycles 3-6, and then every 4 weeks in subsequent cycles until disease progression. |
| Part 1: Cohort 3 | Experimental | Participants will receive DARA PH20 at a dose which will be decide by Study Evaluation Team (SET) once weekly by SC infusion in Cycles 1 and 2, every 2 weeks in Cycles 3-6, and then every 4 weeks in subsequent cycles until disease progression. Also up to three additional optional cohorts (Cohorts 3b, 3c, and 3d) may be enrolled to repeat a dose level of daratumumab |
| Part 2: Cohort 4 | Experimental | DARA PH20 SC infusion at the RP2D (recommended Phase 2 dose) that is identified in Part 1 will be administered to participants by SC infusion once weekly in Cycles 1 and 2, every 2 weeks in Cycles 3-6, and then every 4 weeks in subsequent cycles until disease progression. |
| Part 2: Cohort 5 | Experimental | Daratumumab 1,200 mg will be administered to participants by intravenous (IV) once weekly in Cycles 1 and 2, every 2 weeks in Cycles 3-6, and then every 4 weeks in subsequent cycles until disease progression. |

TABLE 7

| Intervention Name | Type | Associated Arms | Description |
|---|---|---|---|
| Daratumumab Subcutaneous (SC) infusion | Drug | Part 1: Cohort 1 Part 1: Cohort 2 Part 1: Cohort 3 Part 2: Cohort 4 | Participants will receive Daratumumab sc infusion once weekly in Cycles 1 (each cycle is 28 days) and 2, every 2 weeks in Cycles 3-6, and every 4 weeks in subsequent cycles. |
| Recombinant Human Hyaluronidase [rHuPH20]) SC infusion | | Part 1: Cohort 1 Part 1: Cohort 2 Part 1: Cohort 3 Part 2: Cohort 4 | Participants will receive Recombinant Human Hyaluronidase [rHuPH20]) along with Daratumumab by SC infusion once weekly in Cycles 1 (each cycle is 28 days) and 2, every 2 weeks in Cycles 3-6, and every 4 weeks in |
| Daratumumab Intravenous (IV) infusion | | Part 2: Cohort 5 | Participants will receive Daratumumab 1,200 mg IV infusion once weekly in Cycles 1 (each cycle 28 days) and 2, every 2 weeks in Cycles 3-6, and every 4 weeks in subsequent cycles. |

Eligibility

Participants proven to have symptomatic (having symptoms) multiple myeloma (MM) according the IMWG diagnostic criteria:

Measurable disease as defined by any of the following: (a) immunoglobulin (Ig) G myeloma (serum monoclonal-paraprotein [M-protein] level >=1.0 gram/deciliter [g/dL] or urine M-protein level greater than or equal to (>=) 200 milligram[mg]/24 hours[hrs]; or (b) IgA, IgD, or IgE multiple myeloma (serum M-protein level >=0.5 g/dL or urine Mprotein level >=200 mg/24 hrs); or (c) light chain multiple myeloma (serum immunoglobulin free light chain >=10 mg/dL and abnormal serum immunoglobulin kappa lambda free light chain ratio)

Participant must have an Eastern Cooperative Oncology Group (ECOG) performance status score of 0, 1, or 2

Pretreatment clinical laboratory values must meet protocoldefined parameters during the Screening phase Male participant who is sexually active with a woman of child-bearing potential and has not had a vasectomy, must agree to use an adequate contraception method as deemed appropriate by the Investigator, and must also agree to not donate sperm during the study and 4 months after last dose of daratumumab Exclusion Criteria:

Participant has received daratumumab or other anti-cluster of differentiation 38 (anti-CD38) therapies previously Participant has received anti-myeloma treatment within 2 weeks before Cycle 1 Day 1

Participant has previously received an allogenic stem cell transplant; or participant has received autologous stem cell transplantation (ASCT) within 12 weeks before Cycle 1 Day1

Participant has a history of malignancy (other than multiple myeloma) within 5 years before Cycle 1 Day 1 (exceptions are squamous and basal cell carcinomas of the skin and carcinoma in situ of the cervix, or malignancy that in the opinion of the Investigator, with concurrence with the Sponsor's medical monitor, is considered cured with minimal risk of recurrence)

Participant is exhibiting clinical signs of meningeal involvement of multiple myeloma Gender: Both Age limit: 18 years Accepts healthy volunteers: No Interim Readout of Part 1 (Data Cutoff 21 Jul. 2016 for Safety/Demographics/Disease History and 28 Jul. 2016 for the Efficacy Data)

Methods

Patients had RRMM with ≥2 prior lines of therapy including a proteasome inhibitor (PI) and an immunomodulatory drug (IMiD). Part 1 of the 2 part study enrolled sequential cohorts at 1,200 mg and 1,800 mg daratumumab dose levels to determine the recommended SC dose for Part 2. DARA PH20 was administered in 4-week treatment cycles: QW for 8 weeks, Q2W for 16 weeks, and Q4W thereafter. DARA PH20 was infused in 1,200 mg doses in 60 mL over 20 min or 1,800 mg in 90 mL over 30 min, via a syringe pump at rotating sites on the abdomen. Pre- and/or post-infusion medications included paracetamol, diphenhydramine, montelukast, and methylprednisolone. In part 2, pts will be randomized 1:1 to receive the recommended phase 2 dose (RP2D) of SC DARA PH20 or IV daratumumab (16 mg/kg). The RP2D of DARA PH20 will be selected based on a cumulative review of the pharmacokinetic and safety data obtained from part 1 and should achieve a maximum serum Ctrough during weekly dosing that is similar to or higher than that observed for the approved 16 mg/kg IV dose. Primary endpoints were Ctrough of daratumumab up to Cycle 3 Day 1 and safety. Secondary endpoints included overall response rate (ORR).

Results 41 pts were treated in part 1 with SC DARA PH20 at the 1,200 mg (n=8) and 1,800 mg (n=33) dose levels. Infusion related reactions (IRRs) were reported in 9/41 pts (22%) and were mostly grade 1/2 in severity including chills, fever, rigors, vomiting, itching, edema of the tongue, non-cardiac chest pain and wheezing. One patient developed grade 3 dyspnea and 1 patient required hospitalization due to fever and chills (both grade 2) after the first infusion. All IRRs developed during or within 6 hours of the first SC infusion and were controlled with antihistamine, corticosteroid, antiemetic, or bronchodilator treatment. No IRRs were reported with subsequent infusions. Overall, the adverse event profile of DARA-PH20 was consistent with that of IV DARA. Grade 3 or higher drug-related adverse events were reported in 5/41 (12%) pts including fatigue (2 pts), influenza, hypertension, dyspnea, and tumor lysis syndrome. SC administration of DARA PH20 was well tolerated at the abdominal wall injection site with 3/41 (7%) pts reporting grade 1 erythema, induration, or burning sensation. Analysis showed a higher max Ctrough in the 1,800 mg cohort in comparison to the max Ctrough achieved following IV DARA (16 mg/kg).

In the 1,200 mg cohort of 8 pts (median of 5 lines of prior therapy [range 2-10]; prior ASCT, 63%; PI refractory only, 0%; IMiD refractory only, 13%; double refractory to PI and IMiD, 63%) a 25% ORR was observed including 2 partial responses (PR). Median time to response was 14 (range 8-20) weeks. Among 17 response evaluable pts in the 1,800 mg cohort with cycle 3 day 1 assessments (median of 4 prior lines of therapy [[range 2-7]; prior ASCT, 76%; PI refractory only, 6%; IMiD refractory only, 12%; double refractory to PI and IMiD, 65%) a 41% ORR was observed consisting of 3 very good partial responses and 4 PRs. Median time to response was 4 (range 4-8) weeks.

Conclusions:

SC DARA PH20 was well tolerated and achieved serum trough concentrations similar to or greater than IV DARA with a lower rate of IRRs compared to IV DARA over a significantly shorter infusion time. Preliminary data suggest that in this patient population SC DARA-PH20 may enable similar response rates to IV DARA monotherapy. The 1,800 mg dose level of DARA PH20 was selected as the RP2D for part 2 of the study. These early data support further study of SC DARA in clinical trials.

Example 3. Development of Co-Formulations of Daratumumab and Hyaluronidase

Various co-formulations were evaluated in order to establish the overall physico-chemical stability and delivery of daratumumab and rHuPH20 in the co-formulated product. The impact of the concentrations of the active constituent and/or the excipients in the formulations was evaluated in some of the stability and/or animal studies (shelf stability, shaking stability and in pig infusion studies). Table 8 provides a summary of the formulations that have been used in various studies.

TABLE 8

| Formulation | Daratumumab (mg/mL) | rHuPH20 (U/mL) | His (mM) | Sorbitol/ Sucrose (mM) | PS20 (% w/v) | Met (mg/mL) | pH |
|---|---|---|---|---|---|---|---|
| 1 | 100 | 500 | 10 | 300 | 0.04 | 2 | 5.5 |
| 2 | 120 | 2000 | 10 | 300 | 0.04 | 1 | 5.6 |
| 3 | 100 | 500 | 10 | 300 | 0.0 | 2 | 5.5 |
| 4 | 100 | 500 | 10 | 300 | 0.01 | 2 | 5.5 |
| 5 | 100 | 500 | 10 | 300 | 0.02 | 2 | 5.5 |
| 6 | 100 | 500 | 10 | 300 | 0.06 | 2 | 5.5 |
| 7 | 100 | 0 | 10 | 200/100 | 0.04 | 0 | 5.5 |
| 8 | 100 | 0 | 10 | 100/200 | 0.04 | 0 | 5.5 |
| 9 | 100 | 50 | 10 | 300 | 0.04 | 1 | 5.5 |
| 10 | 100 | 500 | 10 | 300 | 0.04 | 1 | 5.5 |
| 11 | 100 | 2000 | 10 | 300 | 0.04 | 1 | 5.5 |
| 12 | 100 | 5000 | 10 | 300 | 0.04 | 1 | 5.5 |

His: histidine
Met: methionine

The ranges of the excipients and the active constituents in the tested formulations are shown in Table 9.

TABLE 9

| Formulation component | Range |
|---|---|
| rHuPH20 | 0-2000 U/mL |
| Daratumumab | 100-120 mg/mL |
| Histidine | 10 mM |
| Sorbitol | 100-300 mM |
| Sucrose | 0-200 mM |
| Polysorbate-20 (PS20) | 0.0-0.04% (w/v) |
| Methionine | 0-2 mg/mL |

The generated formulations were tested in various assays for their characteristics, including evaluation of sub-visible particles, micro flow imaging (MFI), size exclusion chromatography (SEC), capillary iso-electric focusing (cIEF), SDS-PAGE (non-reducing and reducing), peptide mapping, extractable volume, turbidity, osmolality, and pH.

Sub-visible particles (Sub-vis): Number of sub-visible particles sizes of ≥10 μm or ≥25 μm is usually aggregates of protein molecules and can be assayed by the light obscuration HIAC method whereby the solution is passed through a small orifice and the blockage of light provides the information on the particle size passing through.

MFI: An orthogonal to the light obscuration method, micro flow imaging (MFI) takes snapshot images of particles flowing through and re-converts back to the number of particles present in a particular volume of liquid. This method provides information about the large aggregates of proteins present in the solution.

SEC: A size exclusion chromatographic separation method whereby a column is used to distribute the molecules within the solution flowing through according to their broad size range. Monomers, aggregates and fragments elute at different times from the column and hence their relative proportions in a sample can be quantified using a standard UV detector.

cIEF: Capillary iso-electric focusing distributes the molecules according to the charge on the molecule and is a good indicator of the overall chemical stability. For example deamidation may result in a change in the charge of the molecule and thus would be picked up by this method. The method provides an idea of the total acidic, basic and intact % of molecules present in the solution.

SDS (reducing and non-reducing conditions): SDS method provides information on the physical stability of the molecule. SDS provides a measure of the intact, aggregated and fragmented species present in the solution. Non reducing SDS provides information on the respective intact, aggregated and fragmented constituents of the antibody while reducing SDS (after disulfide disruption) provides the same information for the heavy and light chains of the antibody.

Peptide mapping: Peptide mapping is an essential technique for studying the primary structure of proteins. For recombinant protein pharmaceuticals, peptide mapping is used for the initial proof of structure characterization. Peptide mapping also provides information on post translational modifications such as deamidation, oxidation etc Extractable volume: The method provides information on the amount/volume of liquid that can be withdrawn from the vial after the respective time point.

Turbidity: A light scattering based method to evaluate the physical stability of the solution. An increase in the size of the particles or aggregates results in an increase in the light scattering signal and is hence picked up as turbidity (opalescence) of the solution. Turbidity is measured in Nephelometric Turbidity Units (NTU).

Osmolality: Provides a measure of the total osmotic activity which is dependent on the total true activity of the molecules (activity coefficient multiplied by concentration). The solution must be close to the osmolality of the serum to be injectable.

pH: Provides an idea of the overall stability and is important that the pH remains constant throughout the shelf life.

rHuPH20 enzymatic activity: The determination of hyaluronidase activity is based on the formation of a precipitate when hyaluronic acid (HA) binds with acidified serum. The activity is measured by incubating hyaluronidase with HA for 30 minutes in a 96-well plate format at 37° C. and then precipitating the undigested HA with the addition of acidified serum. The resulting turbidity is measured at 640 nm and the decrease in turbidity resulting from enzymatic cleavage of the HA substrate is a measure of the hyaluronidase activity.

Shelf stability of Formulation 1 (100 mg/mL Daratumumab, 10 mM Histidine, 300 mM Sorbitol, 0.04% PS-20, 2 mg/mL Methionine, 500 U/mL PrHuh20, pH 5.5) was evaluated using assays described. Samples were put on stability in 25R vials (filled at 16 mL volume) at different temperatures (5, 25 and 40° C.) and vials were pulled for analysis using various assays at different time points (0, 1, 2, 3, 4, 5 and/or 6 months). Data indicates that the co-formulated product is stable under the storage conditions both with respect to the Daratumumab as well as rHuPH20 as indicated by various assays. The profile as observed for particles, color, turbidity, sec etc was very similar to well behaved stable antibodies and the data is comparable to the stability data of some commercial mAb formulations.

Table 10 shows the number of particles in Formulation 1 over time as assessed using HIAC.

Table 11 shows the number of particles in Formulation 1 over time as assessed using MFI.

Table 12 shows the pH of Formulation 1 over time.

Table 13 shows the turbidity of Formulation 1 over time.

Table 14 shows the proportion of high-molecular weight aggregates and low molecular weight fragments in Formulation 1 over time.

Table 15 shows the acidic and basic species in Formulation 1 over time as assessed using cIEF.

Table 16 shows the percent (%) purity of Formulation 1 over time as assessed using reduced SDS-PAGE.

Table 17 shows the percent (%) purity of Formulation 1 over time as assessed using non-reduced SDS-PAGE.

Table 18 shows the percent (%) bioactivity of daratumumab and enzyme activity of rhPH20 in Formulation 1 over time.

TABLE 10

| Storage Temperature (° C.) | Average Cumulative Count/mL of particle sizes ≥ 10 µM or ≥ 25 µM | | | | | |
|---|---|---|---|---|---|---|
| | 0 months | | 3 months | | 6 months | |
| | ≥10 µm | ≥25 µm | ≥10 µm | ≥25 µm | ≥10 µm | ≥25 µm |
| 5 | 7.17 | 6.33 | 6.5 | 4.8 | 42.50 | 30.83 |
| 25 | 7.17 | 6.33 | 5.5 | 1.8 | 110.50 | 81.83 |
| 40 | 7.17 | 6.33 | 64.5 | 44.8 | | |

TABLE 11

| | 0 months | 3 months | | | 6 months | |
|---|---|---|---|---|---|---|
| | | Temperature (° C.) | | | | |
| | 5 | 5 | 25 | 40 | 5 | 25 |
| Particles/mL ≥2-<10 µm ECD | 539 | 1155 | 3668 | 3371 | 686 | 3581 |
| Particles/mL ≥10-<25 µm ECD | 9.3 | 39 | 93 | 80 | 36 | 105 |
| Particles/mL ≥25-<70 µm ECD | 1.4 | 2.6 | 13 | 9.3 | 7.4 | 7.2 |
| Particles/mL ≥70 µm ECD | 0.5 | 0.2 | 0.2 | 0.2 | 0.0 | 0.5 |

TABLE 12

| Storage Temperature | pH over Storage Time (months) | | | | |
|---|---|---|---|---|---|
| (° C.) | 0 m | 1 m | 2 m | 3 m | 6 m |
| 5 | 5.7 | NA | 5.7 | 5.7 | 5.6 |
| 25 | 5.7 | 5.7 | 5.7 | 5.7 | 5.6 |
| 40 | 5.7 | 5.7 | 5.6 | 5.7 | NA | m: month
NA: not analyzed

TABLE 13

| Storage Temperature | Average NTU over Storage Time (months) | | | | |
|---|---|---|---|---|---|
| (° C.) | 0 m | 1 m | 2 m | 3 m | 6 m |
| 5 | 3.5 | | 3.5 | 3.5 | 3.4 |
| 25 | 3.5 | 3.5 | 3.6 | 3.7 | 4.6 |
| 40 | 3.5 | 4 | 5.5 | 8.2 | NA | m: month
NTU: Nephelometric Turbidity Units
NA: not analyzed

TABLE 14

| Storage Time (months) | Storage Temperature (° C.) | Percentage (%) of species | | |
|---|---|---|---|---|
| | | HMW | Monomer | LMW |
| 0 | 5 | 0.74 | 99.25 | 0.01 |
| | 25 | 0.74 | 99.25 | 0.01 |
| | 40 | 0.74 | 99.25 | 0.01 |
| 3 | 5 | 0.84 | 99.16 | 0.02 |
| | 25 | 1.11 | 98.75 | 0.14 |
| | 40 | 1.87 | 94.50 | 3.64 |
| 6 | 5 | 0.89 | 99.10 | NA |
| | 25 | 1.30 | 98.38 | NA |
| | 40 | NA | NA | NA |

HMW: high molecular weight species
LMW: low molecular weight species
NA: not analyzed

TABLE 15

| Storage Time (months) | Storage Temperature (° C.) | % Main peak | % Acidic peaks | % Basic peaks |
|---|---|---|---|---|
| 0 | 5 | 69.2 | 27.8 | 3 |
| | 25 | 69.2 | 27.8 | 3 |
| | 40 | 69.2 | 27.8 | 3 |
| 3 | 5 | 68.2 | 28.9 | 2.9 |
| | 25 | 63 | 32.8 | 4.2 |
| | 40 | 31.3 | 60.2 | 8.5 |
| 6 | 5 | 68.1 | 28.7 | 3.2 |
| | 25 | 55.4 | 38 | 6.6 |
| | 40 | NA | NA | NA |

NA: not analyzed

TABLE 16

| Storage Temperature | % Purity over Storage Time (in months) | | | | |
|---|---|---|---|---|---|
| (° C.) | 0 m | 1 m | 2 m | 3 m | 6 m |
| 5 | 98.16 | NA | 97.96 | 98 | 98.02 |
| 25 | 98.16 | 97.87 | 97.66 | 97.57 | 96.75 |
| 40 | 98.16 | 96.4 | 95 | 92.88 | NA | m: month
NA: not analyzed

TABLE 17

| Storage Temperature | % Purity over Storage Time (in months) | | | | |
|---|---|---|---|---|---|
| (° C.) | 0 | 1 | 2 | 3 | 6 |
| 5 | 97.56 | | 97.64 | 97.64 | 97.5 |
| 25 | 97.56 | 97.27 | 96.97 | 96.62 | 95.63 |
| 40 | 97.56 | 94.84 | 92.61 | 89.37 | NA | m: month
NA: not analyzed

TABLE 18

| | | | Storage Time and Temperature | |
|---|---|---|---|---|
| Molecule | Assay | 0 months | 6 months 5° C. | 6 months 25° C. |
| Daratumumab | ADCC* | 102 | 103 | 83 |
| | CDC* | 95 | 101 | 93 |
| PH20 | Enzymatic activity** | 574 | 600 or 584? | 609 |

*Percent control
**U/mL

Agitation (shaking) stability of the Formulation 1 was also assessed using the above assays to characterize the formulations and study the impact of PS concentrations by varying just PS-20 concentrations in that formulation (Formulations 1, 3, 4, 5 and 6 in Table 8 where PS-20 was varied to 0, 0.01, 0.02, 0.04, 0.06%). The data indicated that the co-formulation was stable under the shaking conditions both with respect to the Daratumumab as well as the enzyme as indicated by various assays. The profile as observed for particles, color, turbidity, sec etc was very similar to well behaved stable antibodies for all concentrations of PS but 0% (0% PS20 formulation had particles and was not stable) and the data was comparable to the stability data of some commercial mAb formulations (data not shown).

Shelf stability of Formulation 2 (120 mg/mL daratumumab, 10 mM Histidine, 300 mM Sorbitol, 0.04% PS20, 1 mg/mL Methionine, 2000 U/mL rhuPH20, pH 5.5) was evaluated using assays described. Samples were put on stability in 25R vials filled at 13.27 mL volume with overfill (1500 mg dose) at different temperatures and vials were pulled for analysis using various assays as below. The collected data indicated that the co-formulated product is stable under the storage conditions both with respect to the daratumumab as wellrHuPH20. The profile as observed for particles, color, turbidity, sec etc was very similar to well behaved stable antibodies and the data was comparable to the stability data of some commercial mAb formulations. rhuPH20 is very susceptible at higher temperatures and loses all activity very fast when stored at 40° C. Table 19 shows the characteristics of the formulation.

TABLE 19

| | Storage Time, Temperature and relative humidity (RH) | | |
|---|---|---|---|
| Characteristics and/or assay | 0 months 5° C. | 1 month 40° C./ 75% RH | 1 month 25° C./ 60% RH |
| Average Cumulative Count/mL of particle sizes 2-10 μm | 58.89 | 375.68 | 4285.81 |
| Average Cumulative Count/mL of particle sizes 10-25 μm | 3.34 | 12.96 | 1.98 |

TABLE 19-continued

| | Storage Time, Temperature and relative humidity (RH) | | |
|---|---|---|---|
| Characteristics and/or assay | 0 months 5° C. | 1 month 40° C./ 75% RH | 1 month 25° C./ 60% RH |
| Average Cumulative Count/mL of particle sizes ≥ 25 μm | 1.23 | .49 | .12 |
| PS20 (% w/v) | 0.038 | 0.02 | 0.03 |
| pH | 5.6 | 5.6 | 5.6 |
| Turbidity (NTU) | 5 | 11 | 6 |
| % Purity (cSDS, reducing) | 98.4 | 98.6 | 98.1 |
| % AGHC, aglycosylated heavy chain (cSDS, reducing) | 0.4 | 0.5 | 0.4 |
| % Purity (cSDS, non-reducing) | 97.7 | 95.2 | 97.7 |
| % monomer, SE-HPLC | 99.1 | 98.0 | 98.8 |
| % aggregate, SE-HPLC | 0.9 | 1.6 | 1.1 |
| % fragments SE-HPLC | <0.10 | 0.4 | <0.10 |
| Daratumumab bioactivity, CDC (% control) | 105 | 88 | 99 |
| Daratumumab bioactivity, ADCC (% control) | 99 | 73 | 103 |
| rhuPH20 activity (U/mL) | 2205 | 0 | 2258 |

Formulations 3-8 were tested for their shelf stability or shaking stability using some or all assays described. The data indicated that the Formulations 3-8 were stable under the conditions assessed both with respect to the daratumumab as well as HuPH20 (formulations 7 and 8 had no rHuPH20). Methionine was included into formulations 1-6 and 9-12 to provide added oxidation stability. The profile as observed for particles, color, turbidity, sec etc was very similar to well behaved stable antibodies and the data was comparable to the stability data of some commercial mAb formulations (data not shown).

Agitation (shaking) stability of the Formulation 1 was also assessed using the above assays to characterize the formulations and study the impact of PS20 concentrations by varying just PS20 concentrations in that formulation (Formulations 1, 3, 4, 5 and 6 in table 8 where PS20 was varied to 0, 0.01, 0.02, 0.04, 0.06%). The data indicated that the co-formulation was stable under the shaking conditions both with respect to daratumumab as well as rHuPH20 as indicated by various assays. The profile as observed for particles, color, turbidity, sec etc was very similar to well behaved stable antibodies for all concentrations of PS but 0% and the data was comparable to the stability data of some commercial mAb formulations (data not shown).

Formulations 9-12 were also evaluated for the assessment of subcutaneous administration of daratumumab with varying concentrations of enzyme in a swine model as described in Example 2. These studies were conducted to determine a suitable concentration of rhPH20 to deliver 16 mL of daratumumab. End points were infusion pressure, area of swelling or bleb if measurable and qualitative assessment of site. Dose dependent increase in infusion pressure was seen. All rhPH20 concentrations tested (50, 500, 2000, 5000 U/mL were sufficient to deliver 16 mL of daratumumab.

Example 4. Open-Label, Multicenter, Dose Escalation Phase 1b Study to Assess the Subcutaneous (SC) Delivery of Daratumumab in Patients (pts) with Relapsed or Refractory Multiple Myeloma (PAVO)—Readout at Clinical Cut-Off Date 15 Nov. 2016

PAVO study design is described in Example 2. Infusion time was 20 min for 1,200 mg daratumumab and 30 min for 1,800 mg daratumumab (administered with 30,000 U and 45,000 U rHuPH20, respectively).

At clinical cut-off date 15 Nov. 2016, a total of 53 patients were treated with SC DARA-PH20 (daratumumab and rHuPH20) at the 1,200 mg (n=8) and 1,800 mg (n=45) dose levels. Median (range) follow-up was 6.4 (1.6-12.0) months in the 1,200 mg group and 4.3 (0.8-8.6) months in the 1,800 mg group. Median (range) duration of treatment was 2.6 (0.7-12.0) months in the 1,200 mg group and 3.4 (0.7-8.6) in the 1,800 mg group. In the 1,200 mg cohort 88% (n=7) of patients discontinued treatment. Discontinuation of treatment in the 1,200 mg cohort was due to progressive disease (63%, n=5), withdrawal by patient (13%, n=1) or death (13%, n=1). In the 1,800 mg group 33% (n=15) of patients discontinued treatment. Discontinuation of treatment in the 1,800 mg cohort was due to progressive disease (27%, n=12), physician decision (4%, n=2) or death (2%, n=1).

Baseline demographics and clinical characteristics of patients who received 1,200 mg daratumumab and 30,000 U rHuPH20 or 1,800 mg daratumumab and 45,000 U rHuPH20 are shown in Table 20.

TABLE 20

| Characteristic | 1,200 mg daratumumab and 30,000 U rHuPH20 n = 8 | 1,800 mg daratumumab and 45,000 U rHuPH20 n = 45 |
|---|---|---|
| Age, yr | | |
| Median (range) | 66 (49-78) | 63 (36-79) |
| ≥75, % (n) | 13 (1) | 9 (4) |
| Weight, kg | | |
| Median (range) | 75.0 (53.0-82.5) | 74.8 (48.0-133.0) |
| Baseline ECOG performance status, % (n) | | |
| 0 | 25 (2) | 24 (11) |
| 1 | 63 (5) | 73 (33) |
| 2 | 13 (1) | 2 (1) |
| ISS stage, % (n)* | | |
| I | 17 (1) | 47 (21) |
| II | 50 (3) | 33 (15) |
| III | 33 (2) | 20 (9) |
| Median (range) time from diagnosis, yr | 6.55 (1.9-10.3) | 5.94 (1.1-15.2) |
| Prior lines of therapy, % (n) | | |
| Median (range) | 5 (2-10) | 4 (2-11) |
| ≤3 | 38 (3) | 36 (16) |
| >3 | 63 (5) | 64 (29) |
| Prior ASCT, % | 63 (5) | 82 (37) |
| Prior PI, % | 100 (8) | 100 (45) |
| Prior bortezomib | 100 (8) | 96 (43) |
| Prior IMiD, % | 100 (8) | 100 (45) |
| Prior lenalidomide | 100 (8) | 100 (45) |
| Refractory to, % | | |
| PI only | 0 (0) | 4 (2) |
| IMiD only | 13 (1) | 20 (9) |
| Both PI and IMiD | 63 (5) | 58 (26) |
| Last line of therapy | 88 (7) | 71 (32) |

*n = 6 for 1,200 mg group
ECOG, Eastern Cooperative Oncology Group
ISS, International Staging System; ISS stage is derived based on the combination of serum β2-macroglobulin and albumin
ASCT, autologous stem cell transplant
PI, proteasome inhibitor
IMiD, immunomodulatory agent In the 1,200 mg cohort of 8 response evaluable patients, a 25% ORR was observed including 2 PRs. Among 45 response evaluable patients in the 1,800 mg cohort, a 38%

ORR was observed consisting of 1 sCR, 3 VGPRs and 13 PRs. Table 21 shows the overall response rate in each cohort.

TABLE 21

| Response | 1,200 mg n = 8 | 1,800 mg n = 45 |
|---|---|---|
| ORR, % (n) | 25 (2) | 38 (17) |
| sCR | 0 (0) | 2 (1) |
| CR | 0 (0) | 0 (0) |
| VGPR | 0 (0) | 7 (3) |
| PR | 25 (2) | 29 (13) |
| MR | 13 (1) | 11 (5) |
| SD | 50 (4) | 38 (17) |
| PD | 13 (1) | 13 (6) |

Treatment emergent adverse events (TEAE) are shown in Table 22 for the 1,200 mg and the 1,800 mg cohorts. The adverse event profile of the subcutaneous DARZALEX® (daratumumab) and rHuPH20 administration was consistent with that of IV daratumumab administration. No treatment discontinuations occurred due to TEAEs in the 1,800 mg group. Grade 3/4 TEAEs included anemia, thrombocytopenia, neutropenia, lymphopenia, hypertension, fatigue, device-related infection and hyponatremia. Infusion related reactions (IRR) were observed in 13% (n=1) of patients receiving 1,200 mg DARZALEX™ (daratumumab) and 25% (n=11) of patients receiving 1,800 mg DARZALEX™ (daratumumab). IRRs included chills, pyrexia, pruritus, dyspnea, flushing, hypertension, hypotension, nausea, non-cardiac chest pain, oropharyngeal pain, paresthesia, rash, sinus headache, tongue edema, vomiting or wheezing. All IRRs occurred during or within four hours of first infusion and no IRRs were observed during subsequent infusions in either group. All IRRs in the 1,800 mg group were grade 1 or 2. One grade 3 dyspnea was observed in the 1,200 mg group. No grade 4 IRRs were observed in either group.

TABLE 22

| Treatment emergent adverse event (TEAE) | 1,200 mg daratumumab and 30,000 U rHuPH20 n = 8 | 1,800 mg daratumumab and 45,000 U rHuPH20 n = 45 |
|---|---|---|
| Drug-related TEAE, % (n) | 63 (5) | 62 (28) |
| Serious drug-related TEAE, % (n) | 13 (1) | 7 (3) |
| Grade ≥ 3 TEAE, % (n) | 63 (5) | 40 (18) |
| All-grade hematologic TEAEs > 25%, % (n) | | |
| Anemia | 25 (2) | 31 (14) |
| Thrombocytopenia | 38 (3) | 18 (8) |
| All-grade non-hematologic TEAEs > 25%, % (n) | | |
| Upper respiratory tract infection | 38 (3) | 9 (4) |
| Insomnia | 38 (3) | 9 (4) |
| Decreased appetite | 38 (3) | 7 (3) |

Figure 2:
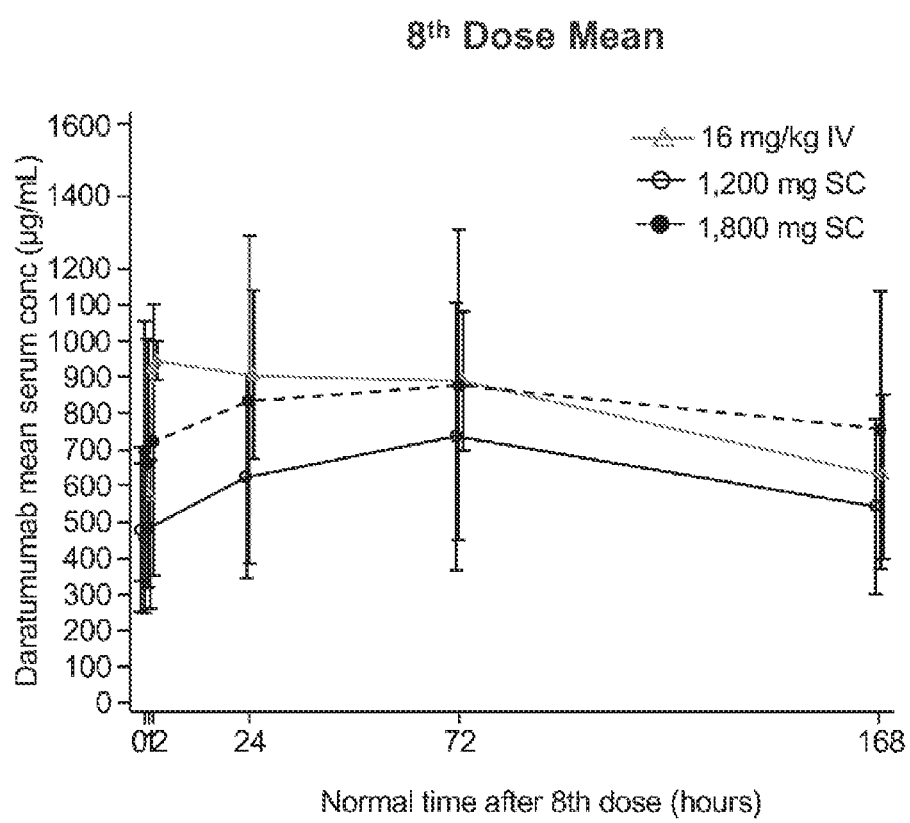
FIG. 2 shows daratumumab mean serum concentration (µg/ml) over time (hours) after administering daratumumab at C3D1 (after 8 weeks of treatment) at 16 mg/kg intravenously (IV), 1,200 mg subcutaneously (SC) or 1,800 mg SC. Vertical bars indicate standard deviation.

Daratumumab serum concentration was assessed up to 168 hours post-dosing after intravenous (16 mg/kg) or subcutaneous (1,200 mg or 1,800 mg) injection after 1$^{st}$ dose at the beginning of treatment (FIG. 1) or 8$^{th}$ dose after 8 week of treatment (FIG. 2) Maximal mean serum concentration was achieved 72 hours post-subcutaneous administration. Subjects with at least one concentration value after the start of daratumumab treatment were included into the analyses. Table 23 shows the comparison of the mean $C_{trough}$ concentration of daratumumab on C3D1 (Cycle 3 Day 1; time-point represents the end of 8 weeks of weekly dosing) in subjects who received 16 mg/kg DARZALEX® (daratumumab) IV (GEN501 Part 2 and SIRIUS trials) or 1,200 mg or 1,800 mg DARZALEX® (daratumumab) SC (PAVO trial). GEN501 Part 2 trial (NCT00574288) evaluated DARZALEX® (daratumumab) as monotherapy in double-refractory MM patients (Lokhorst et al., N Eng J Med 373:1207-19, 2005). SIRIUS (NCT01985126; 54767414MMY2002) evaluated DARZALEX® (daratumumab) in patients with advanced multiple myeloma who received at least 3 prior lines of therapy including a proteasome inhibitor (PI) and an immunomodulatory drug (IMiD) or double refractory to a PI and an IMiD (Clinical Study Report: An Open-label, Multicenter, Phase 2 Trial Investigating the Efficacy and Safety of DARZALEX (daratumumab) in Subjects With Multiple Myeloma Who Have Received at Least 3 Prior Lines of Therapy (Including a Proteasome Inhibitor and IMiD) or are Double Refractory to a Proteasome Inhibitor and an IMiD (EDMS-ERI-92399922; de Weers et al., (2011) J Immunol 186(3):1840-1848). Analysis included all subjects with a concentration value at C3D1 time-point (time-point represents the end of 8 weeks of weekly dosing) regardless of missed doses. In this analysis, variability (% CV) was similar between the SC and IV groups. Mean Ctrough was higher in the 1,800 mg SC group when compared to the 1,200 mg SC and 16 mg/kg IV groups.

TABLE 23

| Study | Dose/route | Number of subjects | Mean $C_{trough}$ (μg/mL) | % CV |
|---|---|---|---|---|
| GEN501 Part 2 | 16 mg/kg IV | 27 | 617.17 | 51% |
| SIRIUS | 16 mg/kg IV | 73 | 573.49 | 58% |
| PAVO | 1,200 mg SC | 5 | 543.90 | 44% |
| | 1,800 mg SC | 41 | 755.27 | 51% |

CV: coefficient of variation
Ctrough: minimum serum concentration after dose administration, and before administration of a subsequent dose.

We claim:

1. A pharmaceutical composition comprising an anti-CD38 antibody at a concentration of about 120 mg/mL and a hyaluronidase at a concentration of about 2000 U/mL, wherein the anti-CD38 antibody is of an IgG1 isotype and comprises a heavy chain variable region sequence of SEQ ID NO: 4 and a light chain variable region sequence of SEQ ID NO: 5, and wherein the hyaluronidase is rHuPH20 (SEQ ID NO: 22).

2. The pharmaceutical composition of claim 1, further comprising a pharmaceutically acceptable carrier.

3. The pharmaceutical composition of claim 1, wherein the anti-CD38 antibody comprises
    a heavy chain sequence of SEQ ID NO: 12 and a light chain sequence of SEQ ID NO: 13.

4. The pharmaceutical composition of claim 2, further comprising
    a) from about 5 mM to about 50 mM histidine; and
    b) from about 50 mM to about 400 mM sorbitol.

5. The pharmaceutical composition of claim 4, further comprising
    a) from about 0.01% w/v to about 0.1% polysorbate-20 (PS-20);
    b) from about 0.1 mg/mL to about 2.5 mg/mL methionine; or
    c) from about 0.01% w/v to about 0.1% PS-20 and from about 0.1 mg/mL to about 2.5 mg/mL methionine.

6. The pharmaceutical composition of claim 4, comprising
    a) about 10 mM histidine; and
    b) from about 100 mM to about 300 mM sorbitol.

7. The pharmaceutical composition of claim 6, further comprising
    a) from about 0.01% w/v to about 0.04% w/v polysorbate-20 (PS-20); and
    b) from about 1 mg/mL to about 2 mg/mL methionine.

8. The pharmaceutical composition of claim 5, comprising
    a) about 10 mM histidine;
    b) about 300 mM sorbitol;
    c) about 0.04% w/v PS-20; and
    d) about 1 mg/mL methionine; pH about 5.6.

9. The pharmaceutical composition of claim 5, comprising
    a) about 10 mM histidine;
    b) about 300 mM sorbitol;
    c) about 0.04% w/v PS-20; and
    d) about 2 mg/mL methionine; pH about 5.5.

10. The pharmaceutical composition of claim 5, comprising
    a) about 10 mM histidine;
    b) about 300 mM sorbitol;
    c) about 0.01% w/v PS-20; and
    d) about 2 mg/mL methionine; pH about 5.5.

11. The pharmaceutical composition of claim 5, comprising
    a) about 10 mM histidine;
    b) about 300 mM sorbitol;
    c) about 0.02% w/v PS-20; and
    d) about 2 mg/mL methionine; pH about 5.5.

12. The pharmaceutical composition of claim 5, comprising
    a) about 10 mM histidine;
    b) about 300 mM sorbitol;
    c) about 0.06% w/v PS-20; and
    d) about 2 mg/mL methionine; pH about 5.5.

13. The pharmaceutical composition of claim 5, comprising
    a) about 10 mM histidine;
    b) about 300 mM sorbitol;
    c) about 0.04% w/v PS-20; and
    d) about 1 mg/mL methionine; pH about 5.5.

14. The pharmaceutical composition of claim 2 which is in a dosage unit form.

15. A method of treating a CD38-positive multiple myeloma (MM) in a subject, comprising administering subcutaneously to the subject in need thereof a pharmaceutical composition comprising an anti-CD38 antibody at a concentration of about 120 mg/ml and a hyaluronidase at a concentration of about 2000 U/ml, for a time sufficient to treat the CD38-positive MM, wherein the anti-CD38 antibody is of an IgG1 isotype and comprises a heavy chain variable region sequence of SEQ ID NO: 4 and a light chain variable region sequence of SEQ ID NO: 5, and wherein the hyaluronidase is rHuPH20 (SEQ ID NO: 22).

16. The method of claim 15, wherein the anti-CD38 antibody comprises a heavy chain sequence of SEQ ID NO: 12 and a light chain sequence of SEQ ID NO: 13.

17. The method of claim 15, wherein the pharmaceutical composition further comprises from about 5 mM to about 50 mM histidine and from about 50 mM to about 400 mM sorbitol, and optionally further comprises from about 0.01% w/v to about 0.1% w/v polysorbate-20 (PS-20), from about 0.1 mg/mL to about 2.5 mg/mL methionine, or from about 0.01% w/v to about 0.1% w/v PS-20 and from about 0.1 mg/mL to about 2.5 mg/mL methionine.

18. The method of claim 17, wherein the pharmaceutical composition comprises about 10 mM histidine and from about 100 mM to about 300 mM sorbitol, optionally further comprising from about 0.01% w/v to about 0.04% w/v PS-20, from about 1 mg/mL to about 2 mg/mL methionine, or from about 0.01% w/v to about 0.04% w/v PS-20 and from about 1 mg/mL to about 2 mg/mL methionine.

19. The method of claim 18, wherein the pharmaceutical composition comprises about 10 mM histidine, about 300 mM sorbitol, about 0.04% w/v PS-20 and about 1 mg/mL methionine; pH about 5.6.

20. The method of claim 18, wherein the pharmaceutical composition comprises about 10 mM histidine, about 300 mM sorbitol, about 0.04% w/v PS-20 and about 2 mg/mL methionine; pH about 5.5.

21. The method of claim 15, further comprising administering a second therapeutic agent.

22. The method of claim 21, wherein the second therapeutic agent is a proteasome inhibitor, an alkylating agent or a glutamic acid derivative, or combinations thereof.

23. The method of claim 22, wherein
a) the proteasome inhibitor is bortezomib, carfilzomib or ixazomib;
b) the alkylating agent is busulfan, cyclophosphamide, bendamustine, chlorambucli, carboplatin, cisplatin, temozolomide, melphalan, carmustine, lomustine, dacarbazine, oxaliplatin, ifosfamide, mechlorethamine, thiotepa, trabectedin or streptozocin; and
c) the glutamic acid derivative is lenalidomide, thalidomide or pomalidomide.

24. The method of claim 23, further comprising administering a corticosteroid.

25. The method of claim 24, wherein the corticosteroid is dexamethasone or prednisone.

26. The method of claim 25, wherein the corticosteroid is dexamethasone.

27. A unit dosage form, comprising
a) an anti-CD38 antibody at a concentration of about 120 mg/mL, wherein the anti-CD38 antibody is of an IgG1 isotype and comprises a heavy chain variable region sequence of SEQ ID NO: 4 and a light chain variable region sequence of SEQ ID NO: 5;
b) a hyaluronidase at a concentration of about 2000 U/mL, wherein the hyaluronidase is rHuPH20 (SEQ ID NO: 22);
c) histidine at a concentration of from about 5 mM to about 15 mM;
d) sorbitol at a concentration of from about 100 mM to about 300 mM;
e) polysorbate-20 (PS-20) at a concentration of from about 0.01% w/v to about 0.04% w/v; and
f) methionine at a concentration of from about 1 mg/mL to about 2 mg/mL, at a pH of about 5.5.

28. The unit dosage form of claim 27, wherein histidine is present at a concentration of about 10 mM.

29. The unit dosage form of claim 28, wherein sorbitol is present at a concentration of about 300 mM.

30. The unit dosage form of claim 29, wherein polysorbate is present at a concentration of about 0.04% w/v.

31. The unit dosage form of claim 30 wherein methionine is present at a concentration of about 1 mg/mL.

32. The unit dosage form of claim 31, optionally comprising sucrose at a concentration of from about 100 mM to about 200 mM.

33. The unit dosage form of claim 32, wherein the anti-CD38 antibody comprises a heavy chain sequence of SEQ ID NO: 12 and a light chain sequence of SEQ ID NO: 13.

34. A container comprising the unit dosage form of claim 33.

35. A unit dosage form, comprising
a) an anti-CD38 antibody at a concentration of about 120 mg/mL, wherein the anti-CD38 antibody is of an IgG1 isotype and comprises a heavy chain variable region sequence of SEQ ID NO: 4 and a light chain variable region sequence of SEQ ID NO: 5;
b) a hyaluronidase at a concentration of about 2000 U/mL, wherein the hyaluronidase is rHuPH20 (SEQ ID NO: 22);
c) histidine at a concentration of about 10 mM;
d) sorbitol at a concentration of about 300 mM;
e) polysorbate-20 (PS-20) at a concentration of about 0.04% w/v; and
f) methionine at a concentration of about 1 mg/mL, at a pH of about 5.6.

36. A container comprising the unit dosage form of claim 35.

37. The unit dosage form of claim 35, wherein the anti-CD38 antibody comprises a heavy chain sequence of SEQ ID NO: 12 and a light chain sequence of SEQ ID NO: 13.

* * * * *